United States Patent
Naidu

(10) Patent No.: US 7,202,370 B2
(45) Date of Patent: Apr. 10, 2007

(54) SEMI-SYNTHESIS OF TAXANE INTERMEDIATES FROM 9-DIHYDRO-13-ACETYLBACCATIN III

(75) Inventor: Ragina Naidu, Burnaby (CA)

(73) Assignee: Conor Medsystems, Inc., Menlo Park, CA (US)

( * ) Notice: Subject to any disclaimer, the term of this patent is extended or adjusted under 35 U.S.C. 154(b) by 197 days.

(21) Appl. No.: 10/695,416

(22) Filed: Oct. 27, 2003

(65) Prior Publication Data

US 2005/0101789 A1 May 12, 2005

(51) Int. Cl.
C07D 305/00 (2006.01)

(52) U.S. Cl. ...................................... 549/510; 549/511

(58) Field of Classification Search ................ 549/510, 549/511
See application file for complete search history.

(56) References Cited

U.S. PATENT DOCUMENTS

| | | | |
|---|---|---|---|
| 4,814,470 A | 3/1989 | Colin et al. | 514/449 |
| 4,924,011 A | 5/1990 | Denis et al. | 549/510 |
| 4,924,012 A | 5/1990 | Colin et al. | 549/510 |
| 4,960,790 A | 10/1990 | Stella et al. | 514/449 |
| 5,136,060 A | 8/1992 | Holton | 549/510 |
| 5,175,315 A | 12/1992 | Holton | 549/510 |
| 5,200,534 A | 4/1993 | Rao | 549/510 |
| RE34,277 E | 6/1993 | Denis et al. | 549/510 |
| 5,229,526 A | 7/1993 | Holton | 549/213 |
| 5,254,703 A | 10/1993 | Holton | 549/510 |
| 5,336,785 A | 8/1994 | Holton | 549/214 |
| 5,350,866 A | 9/1994 | Holton et al. | 549/510 |
| 5,352,806 A | 10/1994 | Gunawardana et al. | 549/510 |
| 5,367,086 A | 11/1994 | Rao | 549/510 |
| 5,405,972 A | 4/1995 | Holton et al. | 549/214 |
| 5,412,116 A | 5/1995 | Murray et al. | 549/379 |
| 5,416,225 A | 5/1995 | Danishefsky et al. | 549/341 |
| 5,422,364 A | 6/1995 | Nicolaou et al. | 514/449 |
| 5,430,160 A | 7/1995 | Holton | 549/510 |
| 5,466,834 A | 11/1995 | Holton | 549/510 |
| 5,468,769 A | 11/1995 | Klein et al. | 514/449 |
| 5,470,866 A | 11/1995 | Kingston et al. | 514/376 |
| 5,475,011 A | 12/1995 | Ojima et al. | 514/320 |
| 5,478,854 A | 12/1995 | Farina et al. | 514/374 |
| 5,489,589 A | 2/1996 | Wittman et al. | 514/232.8 |
| 5,489,601 A | 2/1996 | Holton et al. | 514/337 |
| 5,547,981 A | 8/1996 | Greenwald et al. | 514/449 |
| 5,576,450 A | 11/1996 | Bouchard et al. | 549/510 |
| 5,587,493 A | 12/1996 | Bouchard et al. | 549/510 |
| 5,594,157 A | 1/1997 | Gunawardana et al. | 549/510 |

(Continued)

FOREIGN PATENT DOCUMENTS

EP    0 253 738 B1    1/1990

(Continued)

OTHER PUBLICATIONS

Nikolakakis, A. et al., "*Taxus Canadensis* Abundant Taxane: Conversion to Paclitaxel and Rearrangements," *Bioorganic & Medicinal Chemistry* 8: 1269-1280, 2000.

(Continued)

*Primary Examiner*—Thomas McKenzie
*Assistant Examiner*—Raymond Covington
(74) *Attorney, Agent, or Firm*—Cindy A. Lynch

(57) ABSTRACT

A method is provided for the semi-synthesis of taxane intermediates useful in the preparation of paclitaxel and docetaxel from 9-dihydro-13-acetylbaccatin III. The preparation of a suitably protected baccatin III backbone from 9-dihydro-13-acetylbaccatin III, and the insertion of the phenylisoserine side chain onto the protected baccatin III from 9-dihydro-13-acetylbaccatin III to form the taxane derivatives, paclitaxel and docetaxel is disclosed.

19 Claims, 16 Drawing Sheets

U.S. PATENT DOCUMENTS

Figure 1:
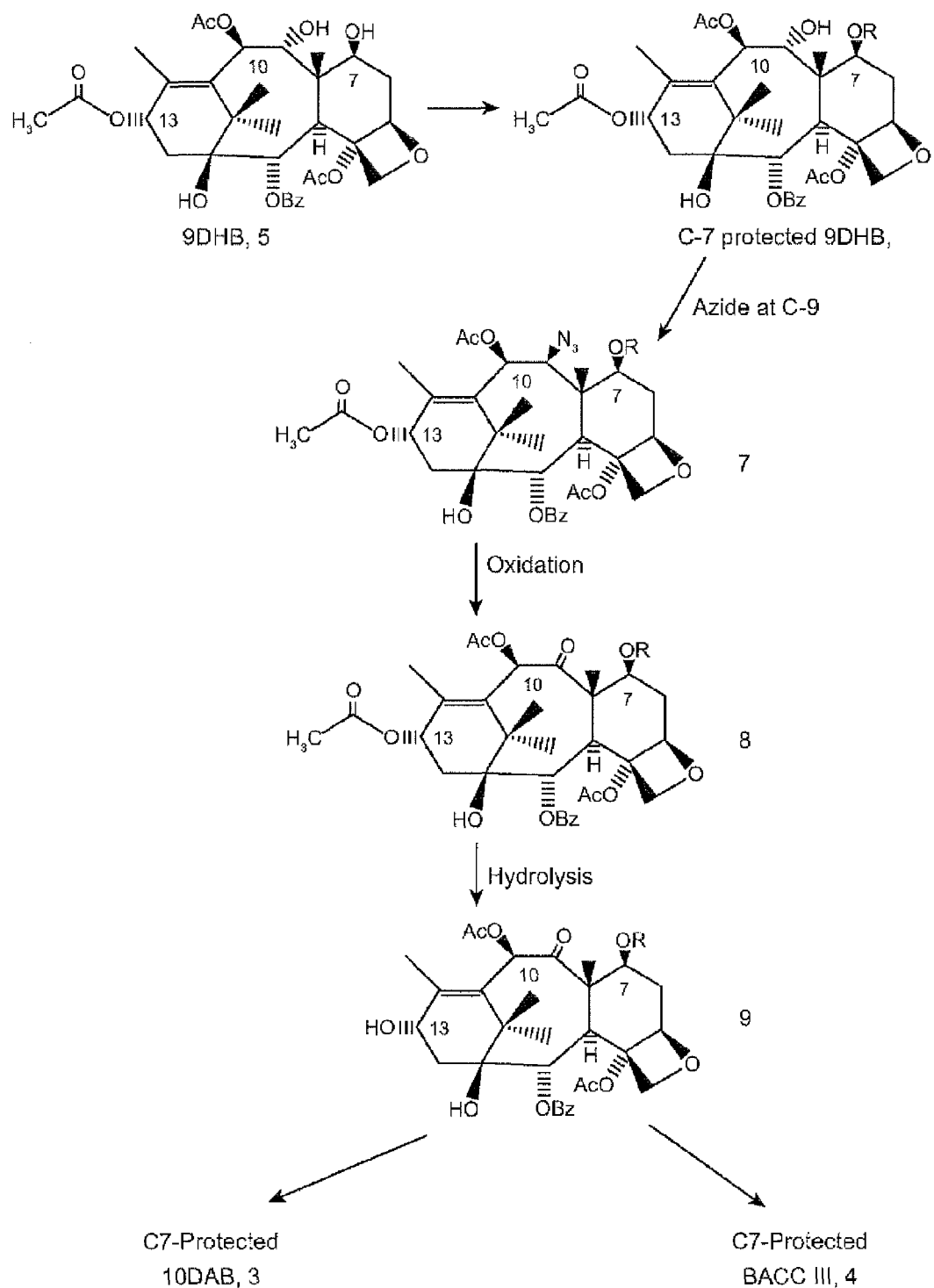

| | | | |
|---|---|---|---|
| 5,606,068 A | 2/1997 | Mas | 548/215 |
| 5,606,083 A | 2/1997 | Bouchard et al. | 549/510 |
| 5,616,739 A | 4/1997 | Mas et al. | 549/510 |
| 5,616,740 A | 4/1997 | Klein et al. | 549/510 |
| 5,621,121 A | 4/1997 | Commercon et al. | 549/510 |
| 5,646,176 A | 7/1997 | Golik et al. | 514/444 |
| 5,654,447 A | 8/1997 | Holton et al. | 549/510 |
| 5,654,449 A | 8/1997 | Bouchard et al. | 549/510 |
| 5,670,658 A | 9/1997 | Bastart et al. | 549/214 |
| 5,688,977 A | 11/1997 | Sisti et al. | 549/510 |
| 5,693,666 A | 12/1997 | Chen et al. | 514/444 |
| 5,703,247 A | 12/1997 | Kingston et al. | 548/962 |
| 5,705,508 A | 1/1998 | Ojima et al. | 514/320 |
| 5,714,513 A | 2/1998 | Holton et al. | 514/449 |
| 5,750,736 A | 5/1998 | Sisti | 549/510 |
| 5,773,461 A | 6/1998 | Wittman et al. | 514/449 |
| 5,780,653 A | 7/1998 | Tao et al. | 549/510 |
| 5,811,452 A | 9/1998 | Ojima et al. | 514/449 |
| 5,874,595 A | 2/1999 | Damen et al. | 549/510 |
| 5,914,411 A | 6/1999 | Sisti et al. | 549/510 |
| 5,965,752 A | 10/1999 | Zamir et al. | 549/510 |
| 6,107,497 A | 8/2000 | Sisti et al. | 549/510 |
| 6,147,234 A | 11/2000 | Holton et al. | 549/510 |
| 6,175,023 B1 | 1/2001 | Liu | 549/510 |
| 6,187,916 B1 | 2/2001 | Ojima | 540/354 |
| 6,197,981 B1 | 3/2001 | Liu | 549/510 |
| 6,218,553 B1 | 4/2001 | Ojima | 549/510 |
| 6,222,053 B1 | 4/2001 | Zamir et al. | 549/510 |
| 6,225,463 B1 | 5/2001 | de Vos et al. | 540/357 |
| 6,262,281 B1 | 7/2001 | Swindell et al. | 549/510 |
| 6,307,088 B1 | 10/2001 | Swindell et al. | 560/27 |
| 6,458,977 B1 | 10/2002 | Holton | 549/510 |
| 6,479,678 B1 | 11/2002 | Holton | 549/510 |
| 6,576,777 B2 | 6/2003 | Zamir et al. | 549/510 |
| 2003/0054977 A1 | 3/2003 | Kumar et al. | 514/2 |

FOREIGN PATENT DOCUMENTS

EP     0 617 018 B1     10/2003

OTHER PUBLICATIONS

Cammercon et al., "Improved Protection and Esterification of a Precursor of the Taxotere and Taxol Side Chains," *Tetrahedron* 33(36):5185-5188,1992.

Cravellee et al., "Methyleniminium Salts as Acylating Agent—One Step Synthesis of Baccatin III from 10-Deacetylbaccatin III with High Selectivity," *Tetrahedron Letters* 39:4263-4266, 1988.

Damen et al., "Lanthanide Trifluoromethanesulfonate Catalysed Selective Acylation of 10-Deacetylbaccatin III," *Tetrahedron Letters 39*: 6081-6082, 1998.

Denis et al., "A Highly Efficient Practical Approach to Natural Taxol," *J. Am. Chem. Soc. 110*:5917-5919, 1988.

Fang et al., "Preliminary Studies on the Acylation of 10.beta-OH and 7.alpha.-OH in 7-epi-10-deacetylpaclitaxel," *Chin. Chem. Lett.* 8(10), Abstract only, 1997.

Georg et al., "Synthesis of Biologically Active Taxol Analogues with Modified Phenylisoserine Side Chains," *J. Med. Chem.* 35:4230-4237, 1992.

Holton et al., "Selective Protection of the C(7) and C(10) Hydroxyl Groups in 10-Deacetyl Baccatin III," *Tetrahedron Letters 39*:2883-2886, 1998.

Kant et al., "A Chemoselective Approach to Functionalize the C-10 position of 10-deacetylbaccatin III. Synthesis and Biological Properties of Novel C-10 Taxol Analogs," *Tetrahedron Letters* 35(31): 5543-5546, 1994.

Kanazawa et al., "Highly Stereocontrolled and Efficient Preparation of the Protected Esterification-Ready Docetaxel (Taxotere) Side Chain", J. Org. Chem. 59(6):1238-1240, 1994.

Klein et al., "Antitumor activity of 9(R)-dihydrotaxane analogs," *J. Med. Chem.* 38(9):1482-1492, Apr. 1995.

McCarthy et al., "Antifungal activity of meridine, a natural product from the marine sponge Corticium sp," *J. Nat. Prod. 55*(11): 1664-1668, Nov. 1992.

Magri et al., "Modified Taxols, 4 Synthesis and Biological Activity of Taxols Modified in the Side Chain," *Journal of Natural Products 51*(2): 298-306, 1988.

Ojima et al., "Efficient and Practical Asymmetric Synthesis of the Taxol C-13 Side Chain, N-Benzoyl-(2R,3S)-3-Phenylisoreine, and its Analogues via Chiral 3-Hydroxy-4-Aryl-β-Lactams Through Chiral Ester Enolate-Imine Cyclocondensation," *J. Org. Chem.* 56(5):1681, 1991.

Ojima et al., "New and Efficient Approaches to the Semisynthesis of Taxol and its C-13 Side Chain Analogs by Means of the B-Lactam Synthon Method", *Tetrahedron 48*(34):6985-7012, 1992.

TAXOTERE, (1)   FIG. 7

SEMI-SYNTHESIS OF TAXANE INTERMEDIATES FROM 9-DIHYDRO-13-ACETYLBACCATIN III

FIELD OF THE INVENTION

The present invention relates to the semi-synthesis of taxane intermediates useful in the preparation of paclitaxel and docetaxel.

BACKGROUND OF THE INVENTION

Docetaxel (1, Taxotere) a semi-synthetic analog and paclitaxel (2, Taxol) a complex diterpene isolated from the bark of *Taxus brefivolia* are arguably the most outstanding cancer chemotherapeutic substances discovered in recent times. While paclitaxel can be obtained from the yew tree or semi-synthetically, only the latter option is currently available for the formation of non-natural docetaxel. The partial synthesis of this important compound has generally been accomplished through esterification of a derivative of the (2R, 3S) phenylisoserine side chain with a protected form of 10-deacetylbaccatin III, a comparatively abundant natural product also present in the yew tree.

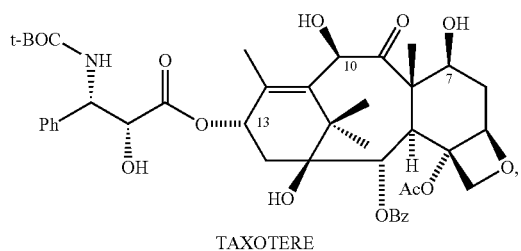

TAXOTERE (1)

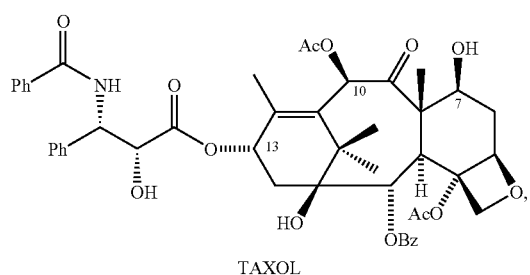

TAXOL (2)

In Colin's U.S. Pat. No. 4,814,470, it was reported that a taxol derivative, commonly referred to as taxotere, has an activity significantly greater than taxol.

Docetaxel and paclitaxel may be prepared semi-synthetically from 10-deacetylbaccatin III or baccatin III as set forth in U.S. Pat. Nos. 4,924,011 and 4,924,012 or by the reaction of a β-lactam and a suitably protected 10-deacetylbaccatin III or baccatin III derivative as set forth in U.S. Pat. No.5,175,315. 10-deacetylbaccatin III (10-DAB, 3) and Baccatin III (4) can be separated from mixtures extracted from natural sources such as the needles, stems, bark or heartwood of numerous *Taxus* species and have the following structures.

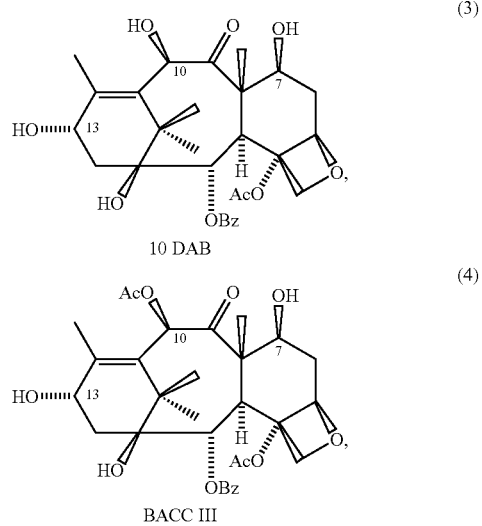

10 DAB (3)

BACC III (4)

Most of the research towards the semi-synthesis of docetaxel and paclitaxel has involved 10-deacetylbaccatin III as the starting material. The conversion of 10-deacetylbaccatin III into either docetaxel or paclitaxel is typically achieved by protecting the hydroxy groups: at C-7 and C-10 positions (for docetaxel) and only C-7 position (for paclitaxel), attachment of an acetyl group at the C-10 position (for paclitaxel), attachment of a C-13 β-amido ester side chain at the C-13 position through esterification of the C-13 alcohol with the β-lactam moiety, and deprotecting at C-7 for paclitaxel and C-7, C-10 for docetaxel.

The research for the semi-synthesis of these two important (docetaxel and paclitaxel) chemotherapeutic agents has been from 10-deacetylbaccatin III because it is the major metabolite present in the European Yew (*Taxus baccata*). However, another abundant taxane, 9-dihydro-13-acetylbaccatin III (9DHB, 5) present in the Canadian Yew (*Taxus Canadensis*) can be utilized for the semi-synthesis of docetaxel and paclitaxel. The present invention demonstrates how to convert 9-dihydro-13-acetylbaccatin III into taxane intermediates: 10-deacetylbaccatin III, baccatin III, docetaxel and paclitaxel.

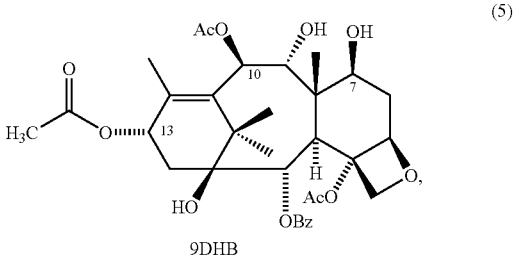

9DHB (5)

BRIEF SUMMARY OF THE INVENTION

The present invention is directed towards providing a novel semi-synthetic route to produce a taxane intermediate, from a naturally occurring taxane 9-dihydro-13-acetylbaccatin III (9DHB, 5) which is present in abundant quantities in *Taxus canadensis*. These intermediates can be used for the preparation of, e.g., docetaxel or paclitaxel.

In one aspect, the present invention provides a compound of the formula

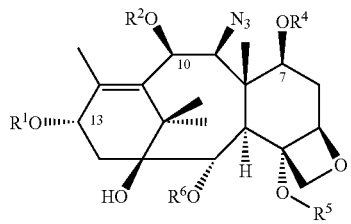

wherein $R^1$, $R^2$, $R^4$, $R^5$ and $R^6$ each represent hydrogen or a hydroxyl protecting group, independently selected at each location. Optionally, for example, $R^1$, $R^2$, $R^4$, $R^5$ and $R^6$ each represent a hydroxyl protecting group. Exemplary hydroxyl protecting groups include, without limitation, formyl, acetyl, dichloroacetyl, propionyl, isopropionyl, pivalyl, trimethylsilyl, triethylsilyl, triisopropylsilyl, dimethylisopropylsilyl, diethylisopropylsilyl, tert-butyldimethylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, t-butyloxycarbonyl, benzyloxycarbonyl, methoxymethyl, methoxyethyl, ethoxyethyl, para-methoxyphenyl, tetrahydropyranyl, tetrahydrofuranyl, alkylsulfonyl or arylsulfonyl.

In another aspect, the present invention provides a method comprising reacting a compound of the formula

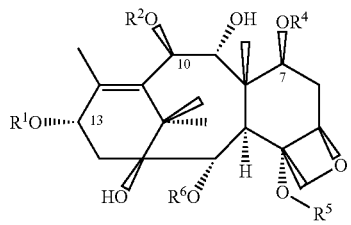

by a Mitsunobu displacement reaction using an azide compound, so as to provide a compound of the formula

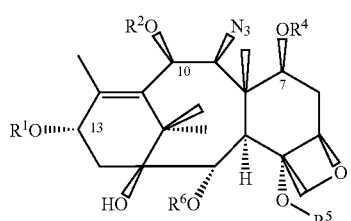

wherein $R^1$, $R^2$, $R^4$, $R^5$ and $R^6$ each represent hydrogen or a hydroxyl protecting group, independently selected at each location. Optionally, for example, the azide compound is diphenylphosphoryl azide or triphenylphosphine/ammonia with the organic base is DBU or DEAD.

In another aspect, the present invention provides a process comprising oxidizing a compound of the formula

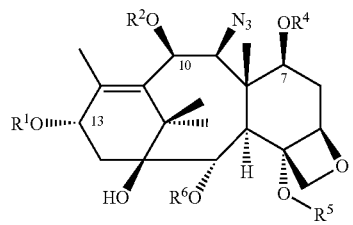

to provide a compound of the formula

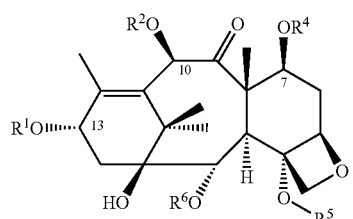

wherein $R^1$, $R^2$ $R^4$, $R^5$ and $R^6$ each represent a hydroxyl protecting group, independently selected at each location. Optionally, the azide is converted to a carbonyl compound by using an alkoxide in THF, most preferably either LiOMe or NaOMe followed by acidic hydrolysis.

In another aspect, the present invention provides a compound of the formula

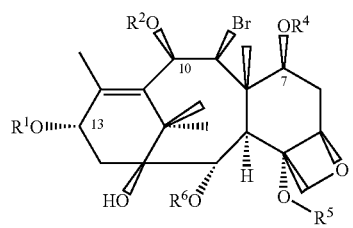

wherein $R^1$, $R^2$, $R^4$, $R^5$ and $R^6$ each represent hydrogen or a hydroxyl protecting group, independently selected at each location. Optionally, e.g., $R^1$, $R^2$, $R^5$ and $R^6$ each represent a hydroxyl protecting group, and $R^4$ is hydrogen. As another optional embodiment, $R^1$ is acetyl, $R^2$ is acetyl, $R^4$ is hydrogen, $R^5$ is acetyl, and $R^6$ is benzoyl.

In another aspect, the present invention provides a process comprising bromination of a compound of the formula

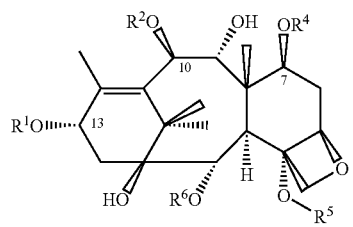

to provide a compound of the formula

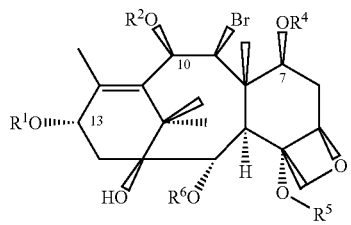

wherein $R^1$, $R^2$, $R^4$, $R^5$ and $R^6$ each represent hydrogen or a hydroxyl protecting group, independently selected at each location. Optionally, the product compound of the compound of the formula

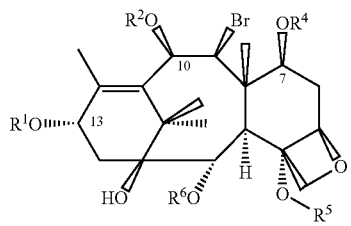

is in admixture with a compound of formula

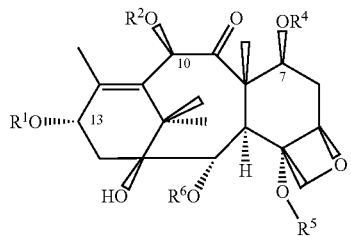

wherein $R^1$, $R^2$, $R^4$, $R^5$ and $R^6$ each represent hydrogen or a hydroxyl protecting group, independently selected at each location.

In another aspect, the present invention provides a process comprising oxidation of a compound of the formula

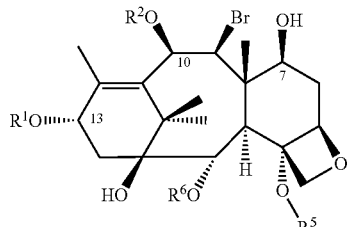

to provide a compound of the formula

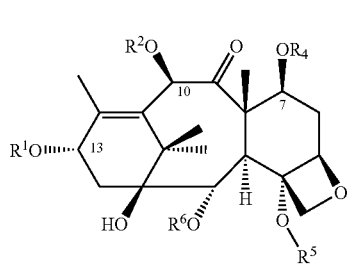

wherein $R^1$, $R^2$, $R^4$, $R^5$ and $R^6$ each represent hydrogen or a hydroxyl protecting group, independently selected at each location. Optionally, for example, a bromide is converted to an azide and the azide is converted to a carbonyl.

In another aspect, the present invention provides a process comprising oxidation of a compound of the formula

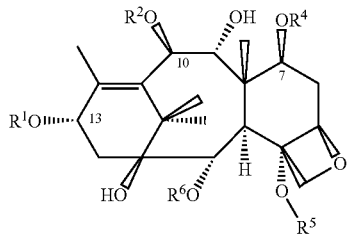

with oxidation conditions comprising $MnO_2$ or DCC/DMSO, to provide a compound of the formula

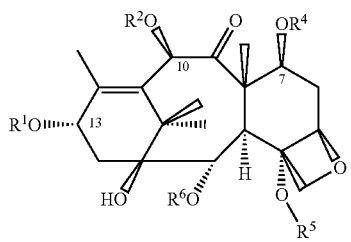

wherein $R^1$, $R^2$, $R^4$, $R^5$ and $R^6$ each represent hydrogen or a hydroxyl protecting group, independently selected at each location.

In another aspect, the present invention provides a compound of the formula

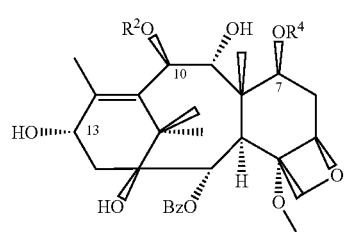

wherein $R^2$ and $R^4$ are identical and selected from triethylsilyl, dichloroacetyl, benzyloxycarbonyl, and 2,2,2-trichloroethoxycarbonyl.

In another aspect, the present invention provides a process comprising coupling a compound of formula

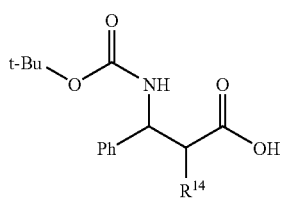

where $R^{14}$ is selected from —SPh, —OAc, —OMe, —OEE, —O-t-BOC, or —OC(O)CH$_2$Cl, with a compound of formula

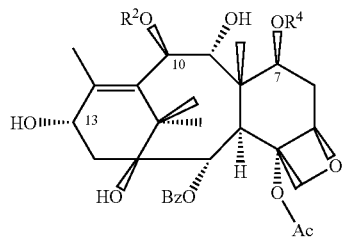

wherein $R^2$ and $R^4$ are identical and selected from triethylsilyl, dichloroacetyl, benzyloxycarbonyl, and 2,2,2-trichloroethoxycarbonyl, to provide a compound of formula

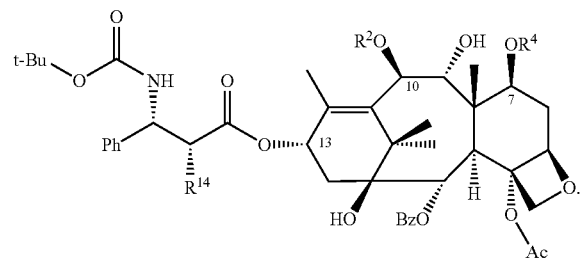

In another aspect, the present invention provides a compound of formula

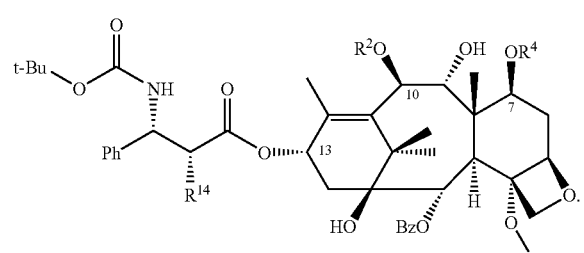

wherein $R^2$ and $R^4$ are identical and selected from triethylsilyl, dichloroacetyl, benzyloxycarbonyl, and 2,2,2-trichloroethoxycarbonyl.

In another aspect, the present invention provides a process comprising coupling a compound of formula

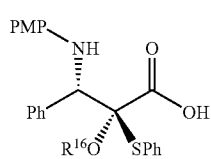

wherein $R^{16}$ is acetyl or ethoxyethyl, with a compound of formula

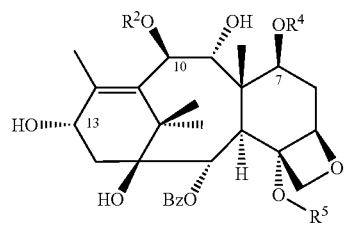

wherein $R^2$ and $R^4$ are identical and selected from triethylsilyl, dichloroacetyl, benzyloxycarbonyl, and 2,2,2-trichloroethoxycarbonyl, to provide a compound of formula

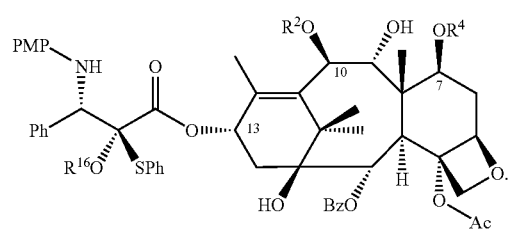

In another aspect, the present invention provides a compound of formula

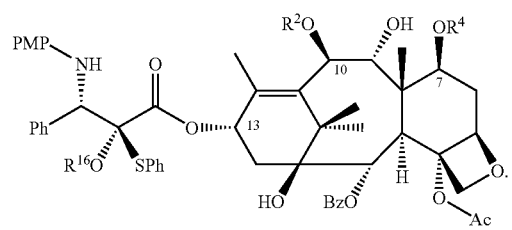

wherein $R^2$ and $R^4$ are identical and selected from triethylsilyl, dichloroacetyl, benzyloxycarbonyl, and 2,2,2-trichloroethoxycarbonyl, and $R^{16}$ is acetyl or ethoxyethyl.

In another aspect, the present invention provides a compound of the formula

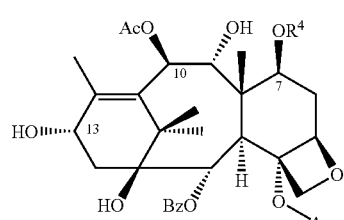

wherein $R^4$ is selected from triethylsilyl, dichloroacetyl, benzyloxycarbonyl, and 2,2,2-trichloroethoxycarbonyl.

In another aspect, the present invention provides a process comprising coupling a compound of formula

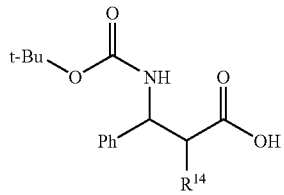

where $R^{14}$ is selected from —SPh, —OAc, —OMe, —OEE, —O-t-BOC, or —OC(O)CH$_2$Cl, with a compound of formula

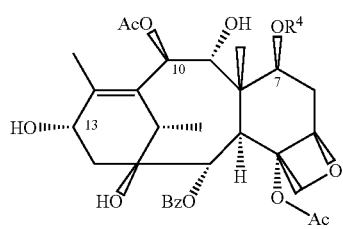

wherein $R^4$ is selected from triethylsilyl, dichloroacetyl, benzyloxycarbonyl, and 2,2,2-trichloroethoxycarbonyl, to provide a compound of formula

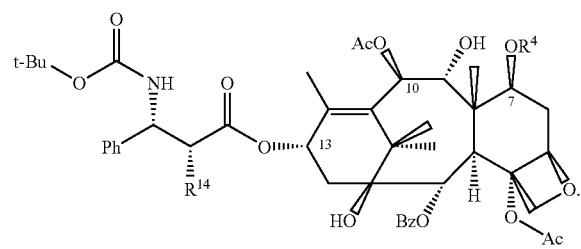

In another aspect, the present invention provides a compound of formula

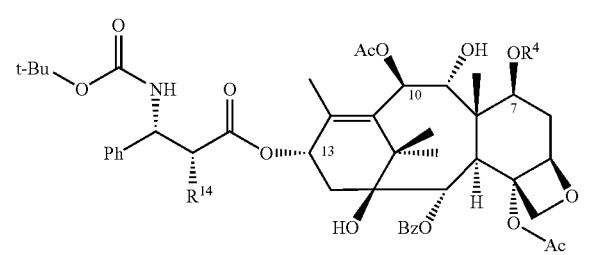

wherein $R^4$ is selected from triethylsilyl, dichloroacetyl, benzyloxycarbonyl, and 2,2,2-trichloroethoxycarbonyl, and $R^{14}$ is selected from —SPh, —OAc, —OMe, —OEE, —O-t-BOC, or —OC(O)CH$_2$Cl.

In another aspect, the present invention provides a process comprising coupling a compound of formula

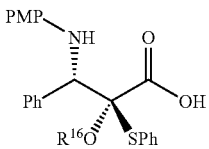

with a compound of formula

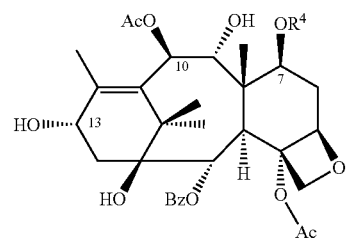

wherein $R^4$ is selected from triethylsilyl, dichloroacetyl, benzyloxycarbonyl, and 2,2,2-trichloroethoxycarbonyl, and $R^{16}$ is selected from acetyl and ethoxyethyl, to provide a compound of formula

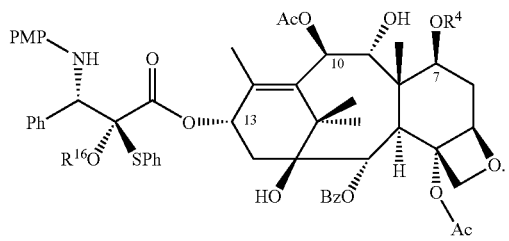

In another aspect, the present invention provides a compound of the formula

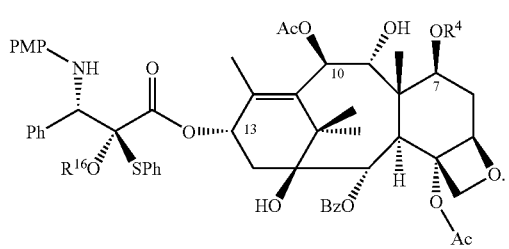

wherein $R^4$ is selected from triethylsilyl, dichloroacetyl, benzyloxycarbonyl, and 2,2,2-trichloroethoxycarbonyl, and $R^{16}$ is selected from acetyl and ethoxyethyl.

In another aspect, the present invention provides a compound of the formula

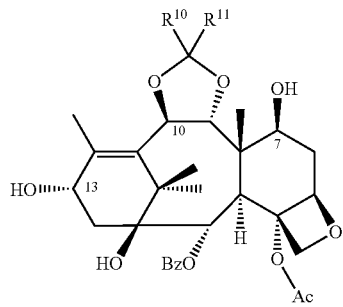

wherein $R^{10}$ and $R^{11}$ are independently selected from alkyl groups.

In another aspect, the present invention provides a process comprising coupling a compound of formula

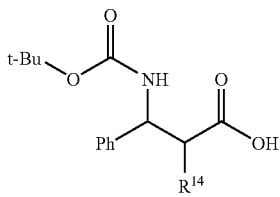

where $R^{14}$ is selected from —SPh, —OAc, —OMe, —OEE, —O-t-BOC, or —OC(O)CH$_2$Cl, with a compound of formula

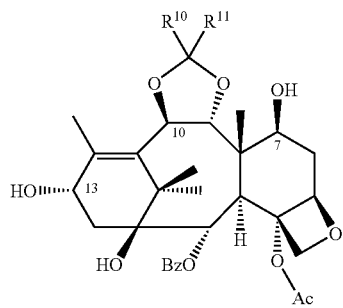

wherein $R^{10}$ and $R^{11}$ are independently selected from alkyl groups, to provide a compound of formula

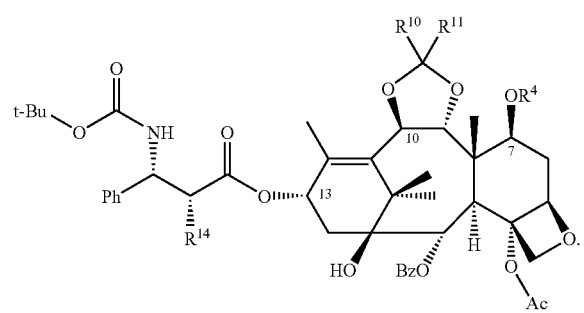

In another aspect, the present invention provides a compound of the formula

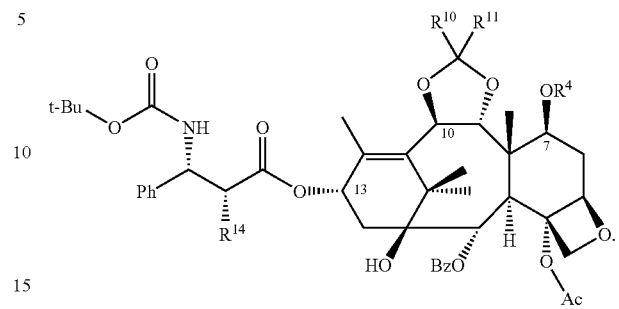

wherein $R^4$ is hydrogen or a hydroxyl protecting group, $R^{10}$ and $R^{11}$ are independently selected from alkyl groups, and $R^{14}$ is selected from —SPh, —OAc, —OMe, —OEE, —O-t-BOC, or —OC(O)CH$_2$Cl.

In another aspect, the present invention provides a process comprising coupling a compound of formula

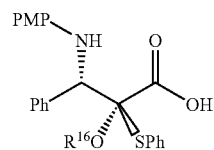

wherein $R^{16}$ is acetyl or ethoxyethyl, with a compound of formula

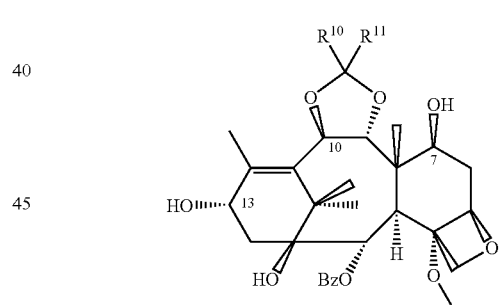

wherein $R^{10}$ and $R^{11}$ are independently selected from alkyl groups, to provide a compound of formula

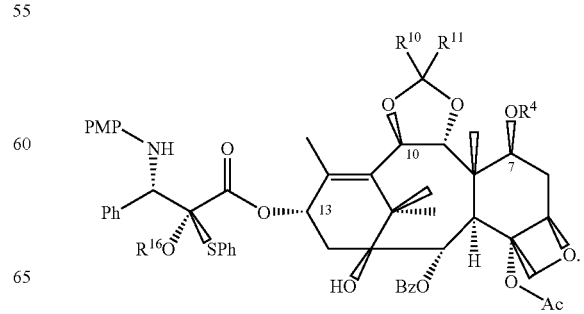

In another aspect, the present invention provides a compound of formula

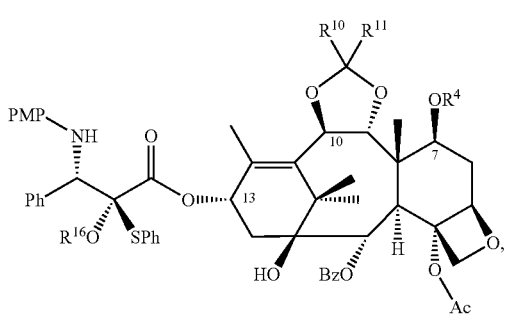

wherein $R^4$ is hydrogen or a hydroxyl protecting group, $R^{10}$ and $R^{11}$ are independently selected from alkyl groups, and $R^{16}$ is acetyl or ethoxyethyl.

In another aspect, the present invention provides a process comprising reacting an imine of formula Ph-CH=N—$R^{13}$ wherein $R^{13}$ represents hydrogen or an amine protecting group, with a C13 acetate ester of Baccatin or a derivative or analog thereof of formulae

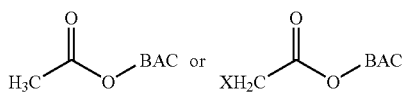

wherein X is a halide, to provide a coupled product of formula

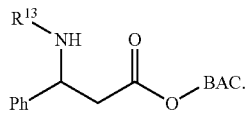

In another aspect, the present invention provides a process comprising treating a starting compound of the formula

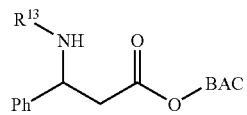

wherein $R^{13}$ represents hydrogen or an amine protecting group, under diazotiation conditions, to provide a product compound of the formula

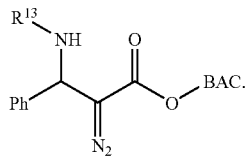

Optionally, for example, the starting compound is

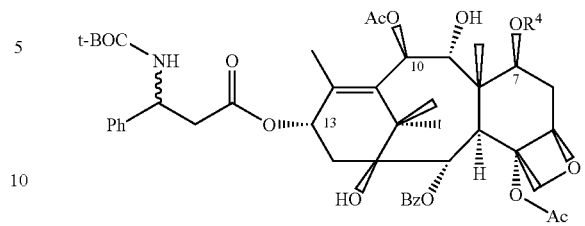

where $R^4$ is hydrogen or a hydroxyl protecting group, and the product compound is

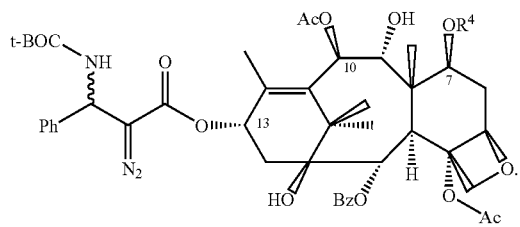

In another aspect, the present invention provides a process comprising treating a compound of the formula

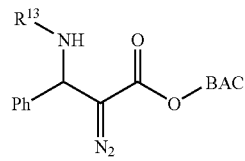

where $R^{13}$ is hydrogen or an amine protecting group, under conditions that convert a diazo group to an acetate group, to provide a compound of the formula

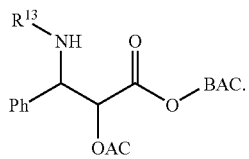

In another aspect, the present invention provides a process comprising treating a compound of the formula

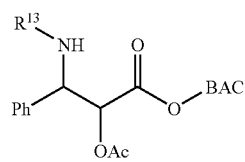

where $R^{13}$ is hydrogen or an amine protecting group, under hydrolysis conditions that (a) convert an acetate group to a hydroxyl group, or (b) convert an acetate group to an ethoxyethyl group and then the ethoxyethyl group to a hydroxyl group, and provide a compound of the formula

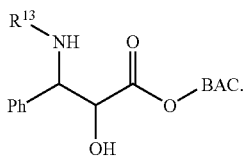

In another aspect, the present invention provides a process comprising treating a compound of the formula

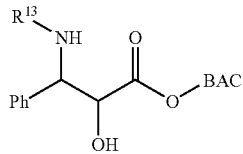

where $R^{13}$ is an amine protecting group, under conditions that remove an amine protecting group and provide a compound of the formula

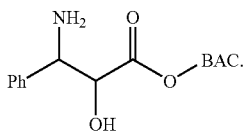

In another aspect, the present invention provides a process comprising treating a compound of the formula

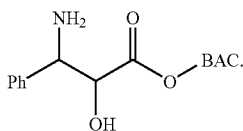

under conditions that introduce a benzoyl group and provide a compound of the formula

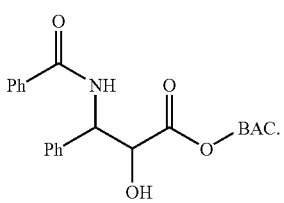

In another aspect, the present invention provides a process comprising exposing a compound of the formula

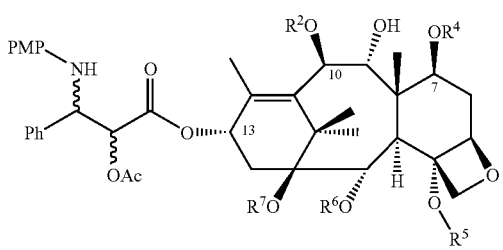

to oxidation conditions, to provide the corresponding ketone of the formula

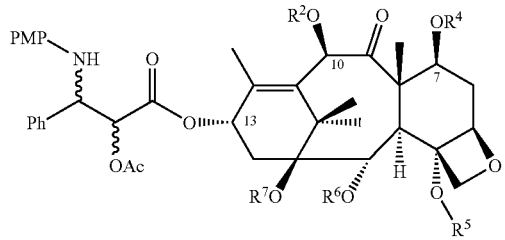

wherein $R^2$ is a hydroxyl protecting group, $R^4$ is a hydroxyl protecting group, $R^5$ is a hydroxyl protecting, $R^6$ is a hydroxyl protecting group.

In another aspect, the present invention provides a process comprising enolate oxidation of a starting compound of the formula

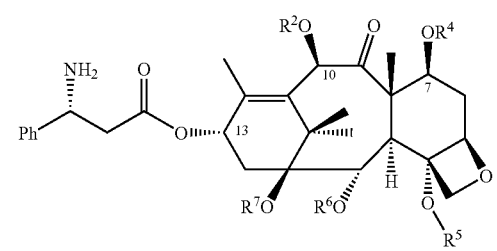

to provide a product compound of the formula

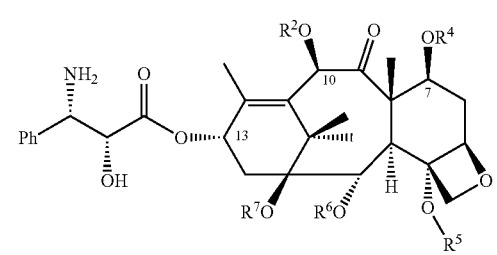

wherein $R^2$ is a hydroxyl protecting group, $R^4$ is hydrogen or a hydroxyl protecting group, $R^5$ is a hydroxyl protecting group, $R^6$ is a hydroxyl protecting group, and $R^7$ is hydrogen or a hydroxyl protecting group.

In another aspect, the present invention provides a process comprising coupling a beta lactam of the formula

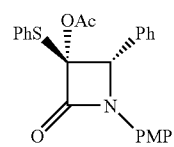

with a baccatin compound of the formula

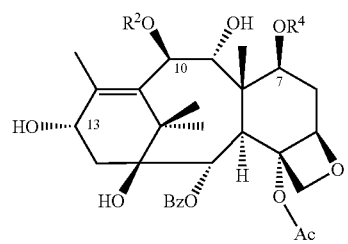

wherein $R^2$ and $R^4$ are both TES or are both dichloroacetyl, or $R^2$ is acetyl and $R^4$ is TES or dichloroacetyl.

In another aspect, the present invention provides a process of preparing a taxane comprising the reaction sequence

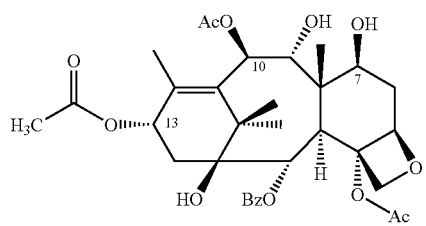

↓

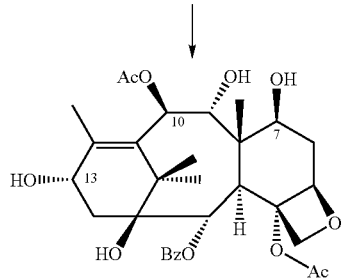

↓

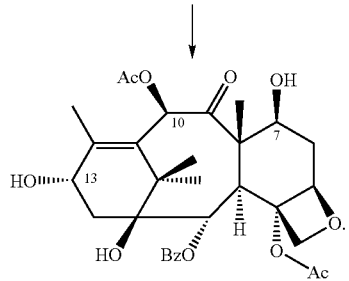

In another aspect, the present invention provides a process of preparing a taxane comprising the reaction sequence

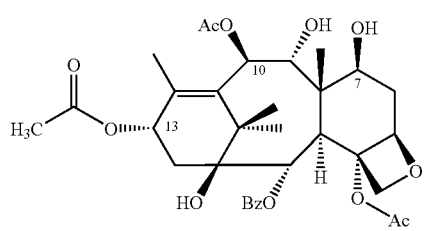

↓

-continued

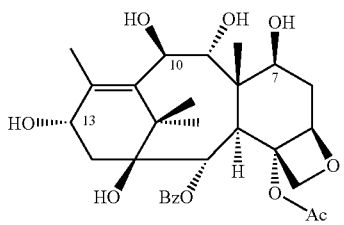

↓

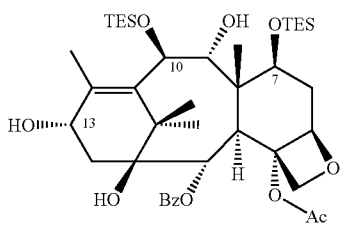

In another aspect, the present invention provides a process of preparing a taxane comprising the reaction sequence

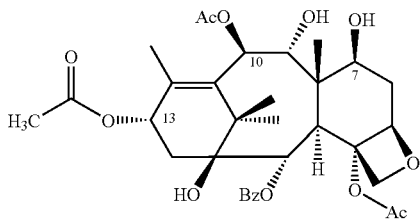

↓

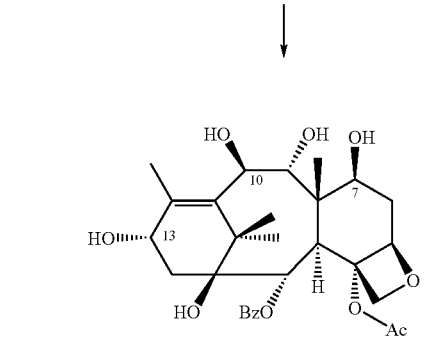

↓

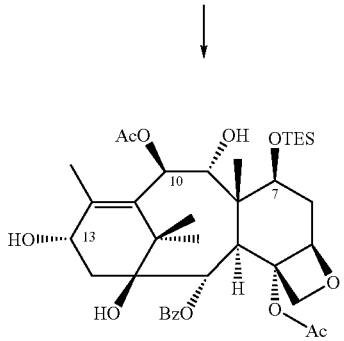

In another aspect, the present invention provides a process of preparing a taxane comprising the reaction sequence

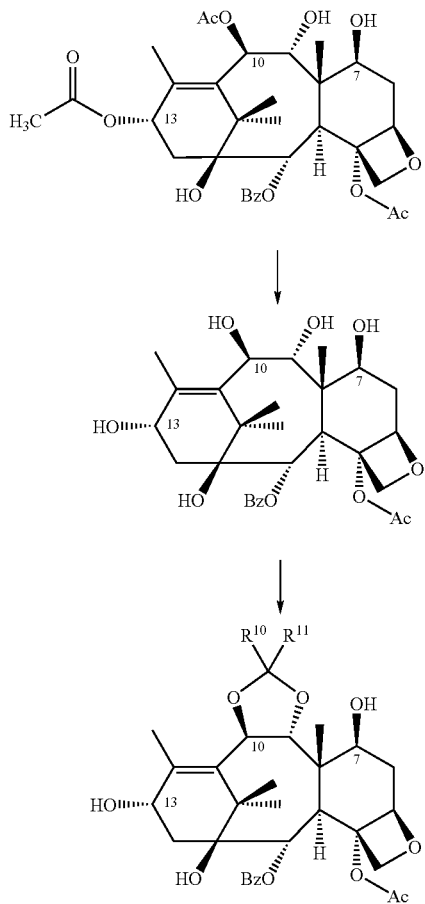

wherein $R^{10}$ and $R^{11}$ are alkyl groups, independently selected at each occurrence.

In another aspect, the present invention provides a process of preparing a taxane comprising the reaction sequence

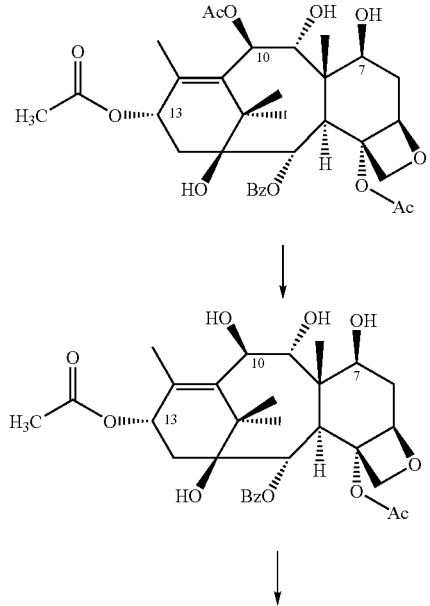

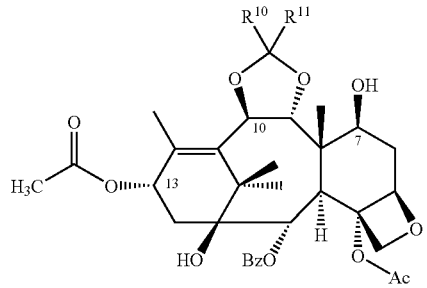

wherein $R^{10}$ and $R^{11}$ are alkyl groups, independently selected at each occurence.

These and other aspects of the present invention are described in further detail below.

BRIEF DESCRIPTION OF THE SEVERAL VIEWS OF THE DRAWING(S)

Figure 2:
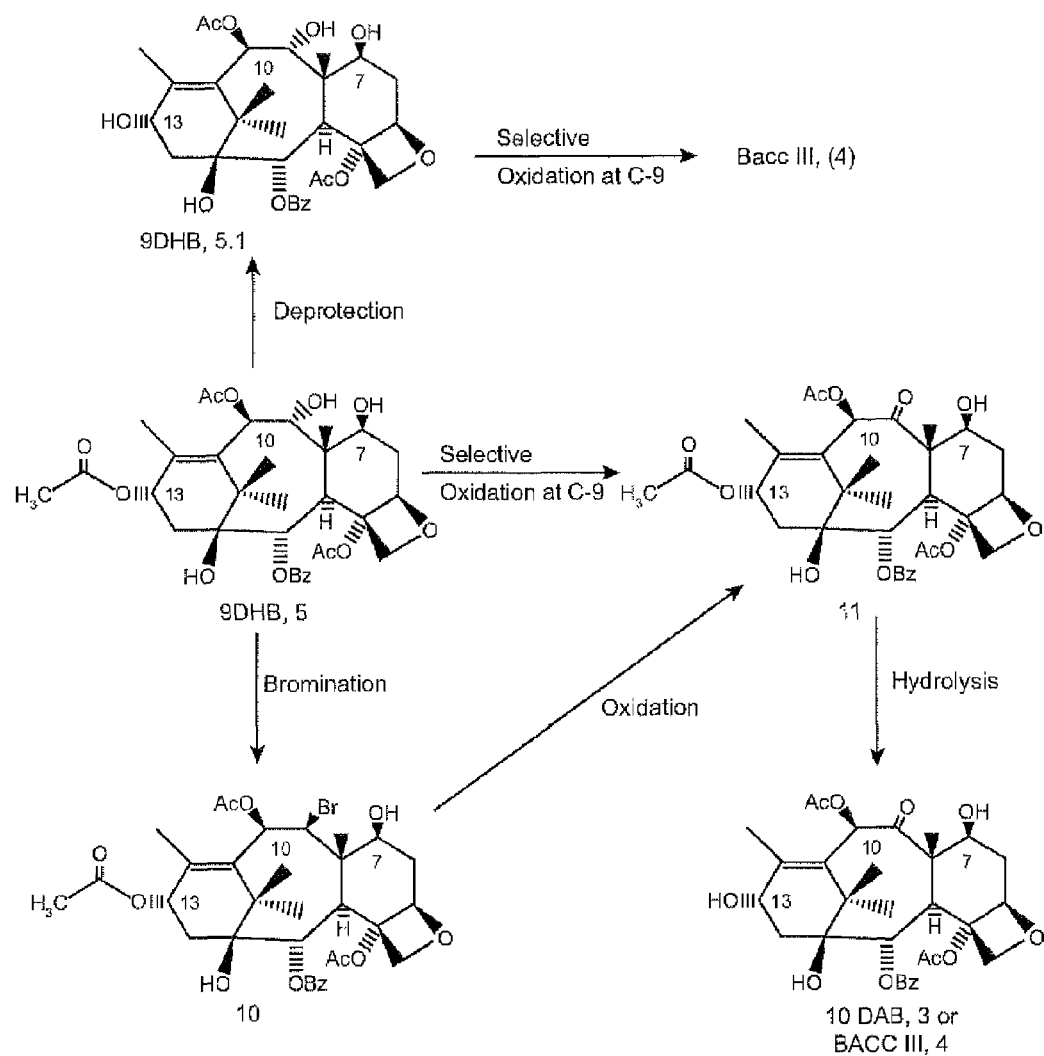
Figure 3:
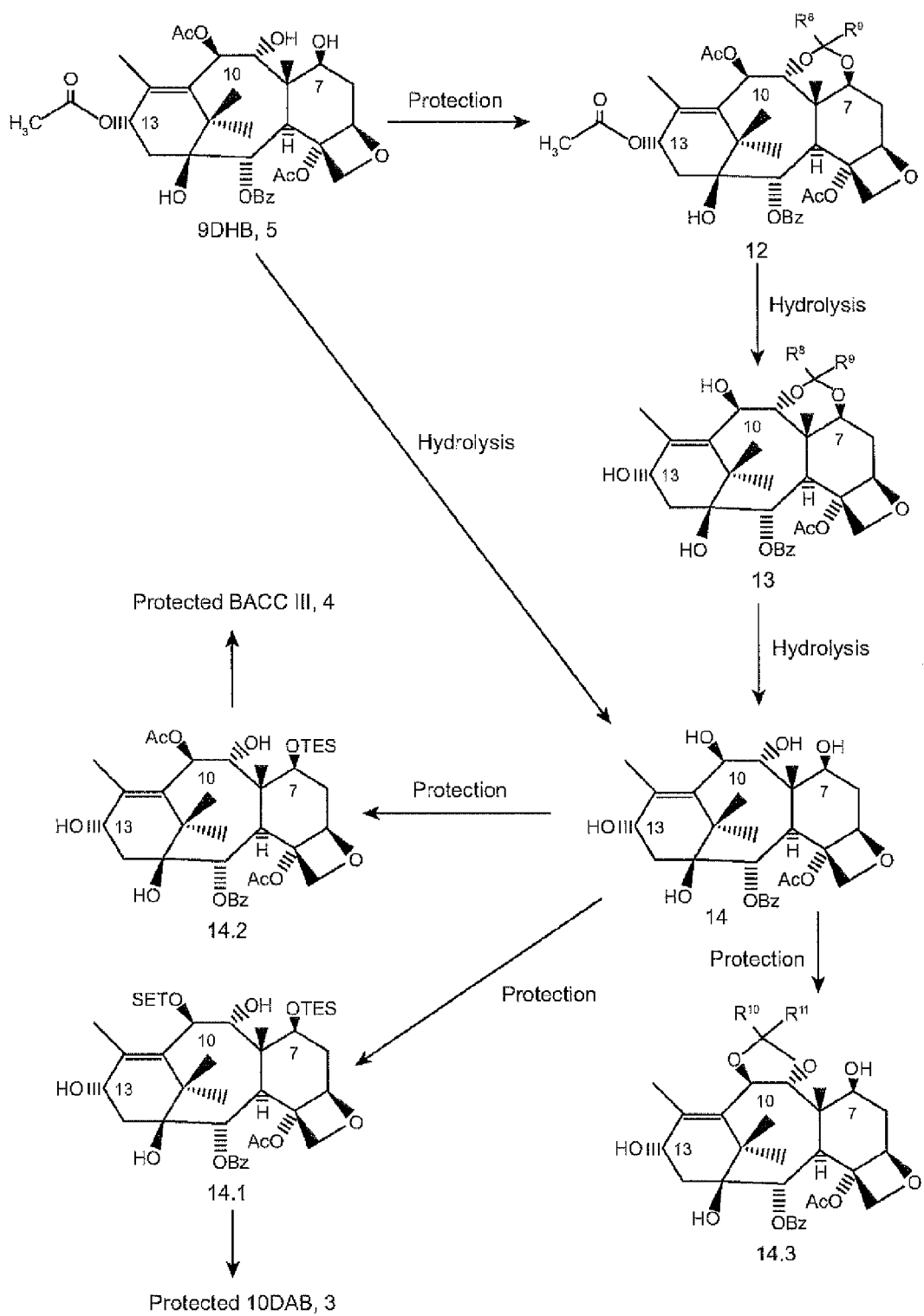
Figure 3A:
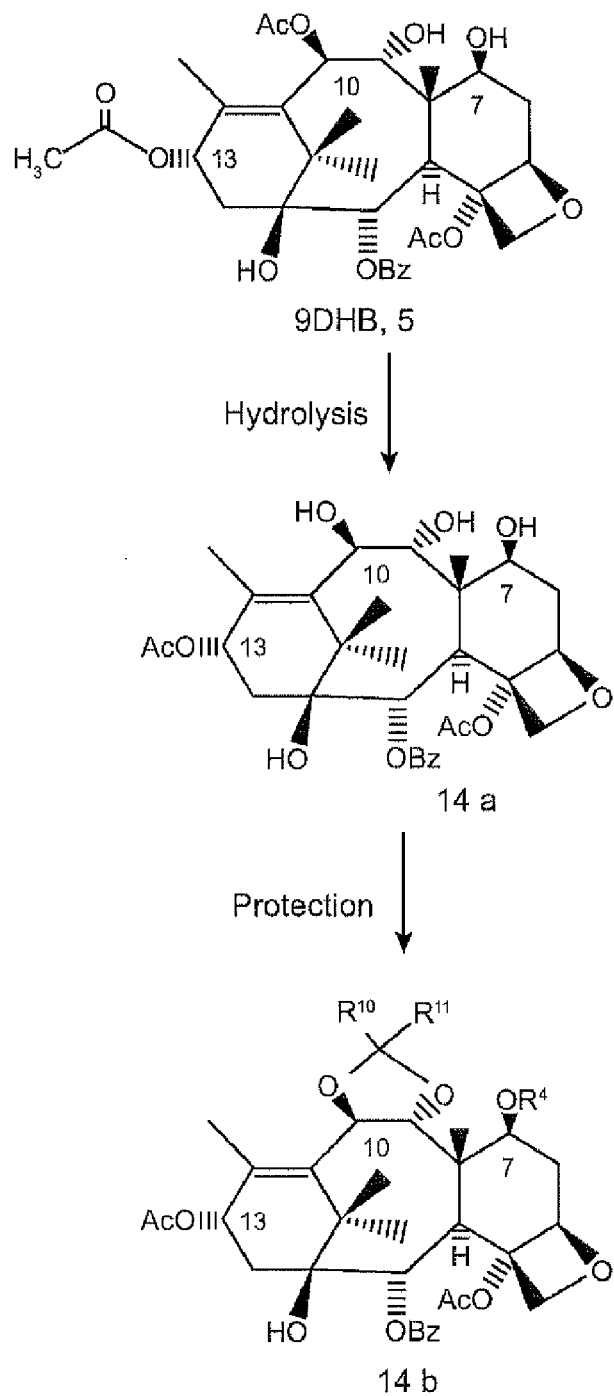
Figure 4:
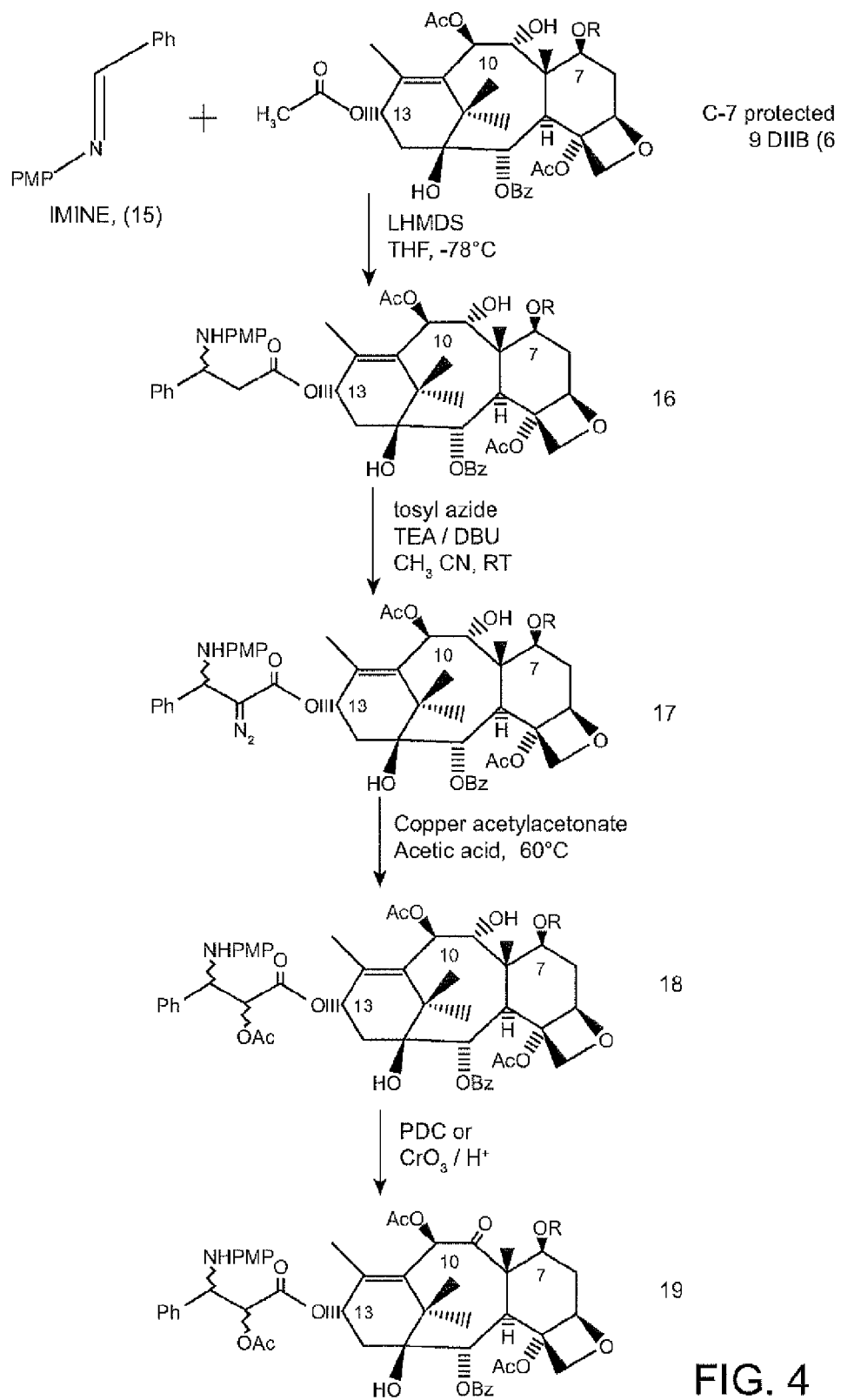
Figure 5:
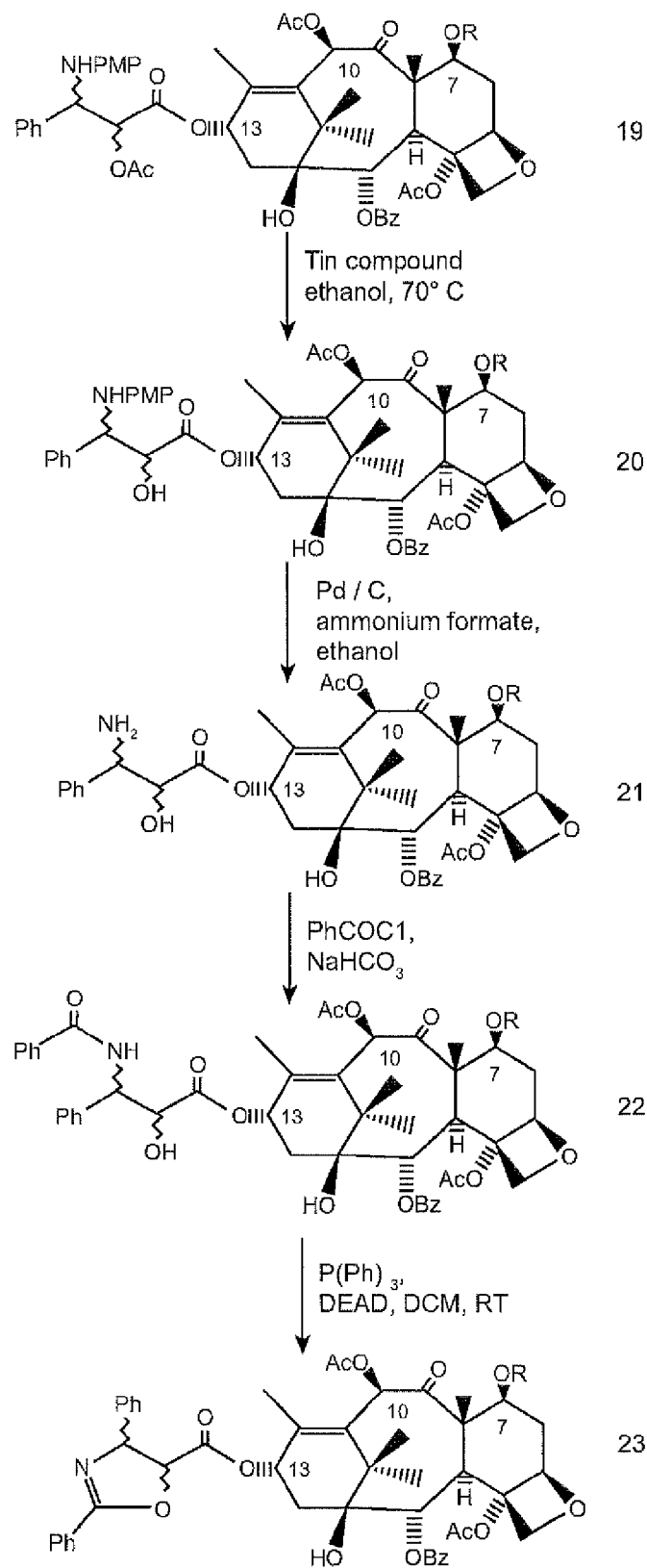
Figure 6:
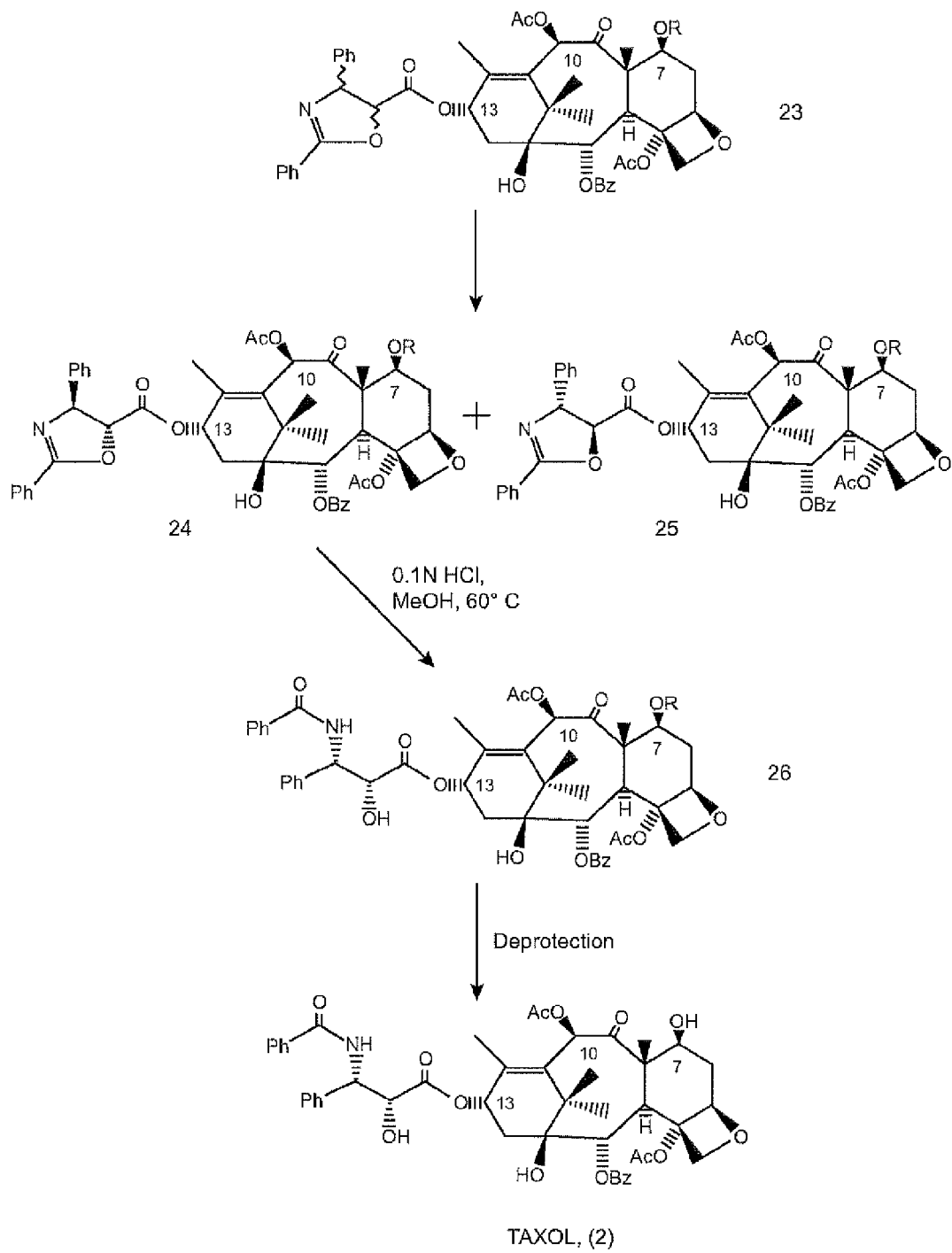
Figure 7:
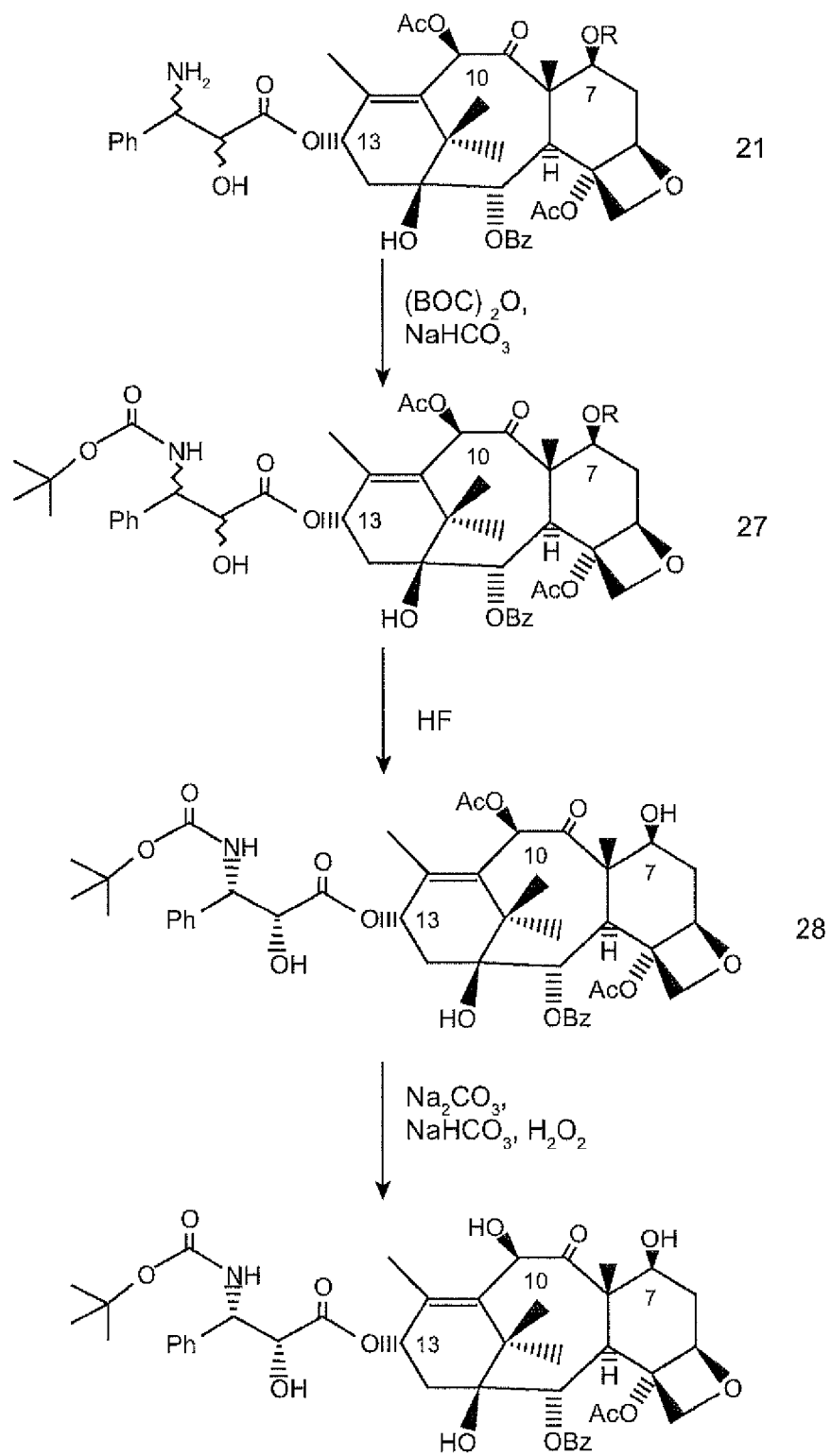
Figure 8:
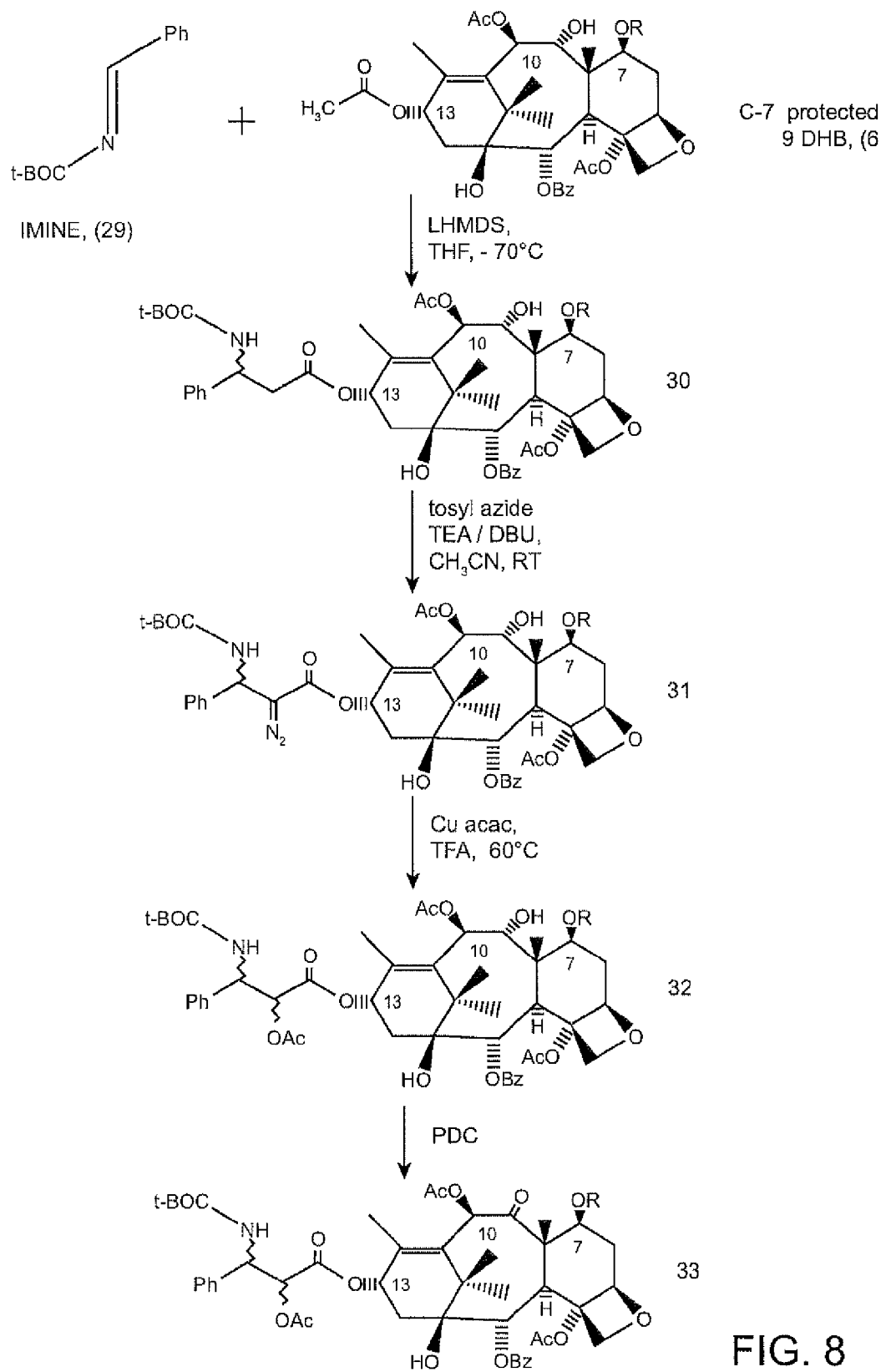
Figure 9:
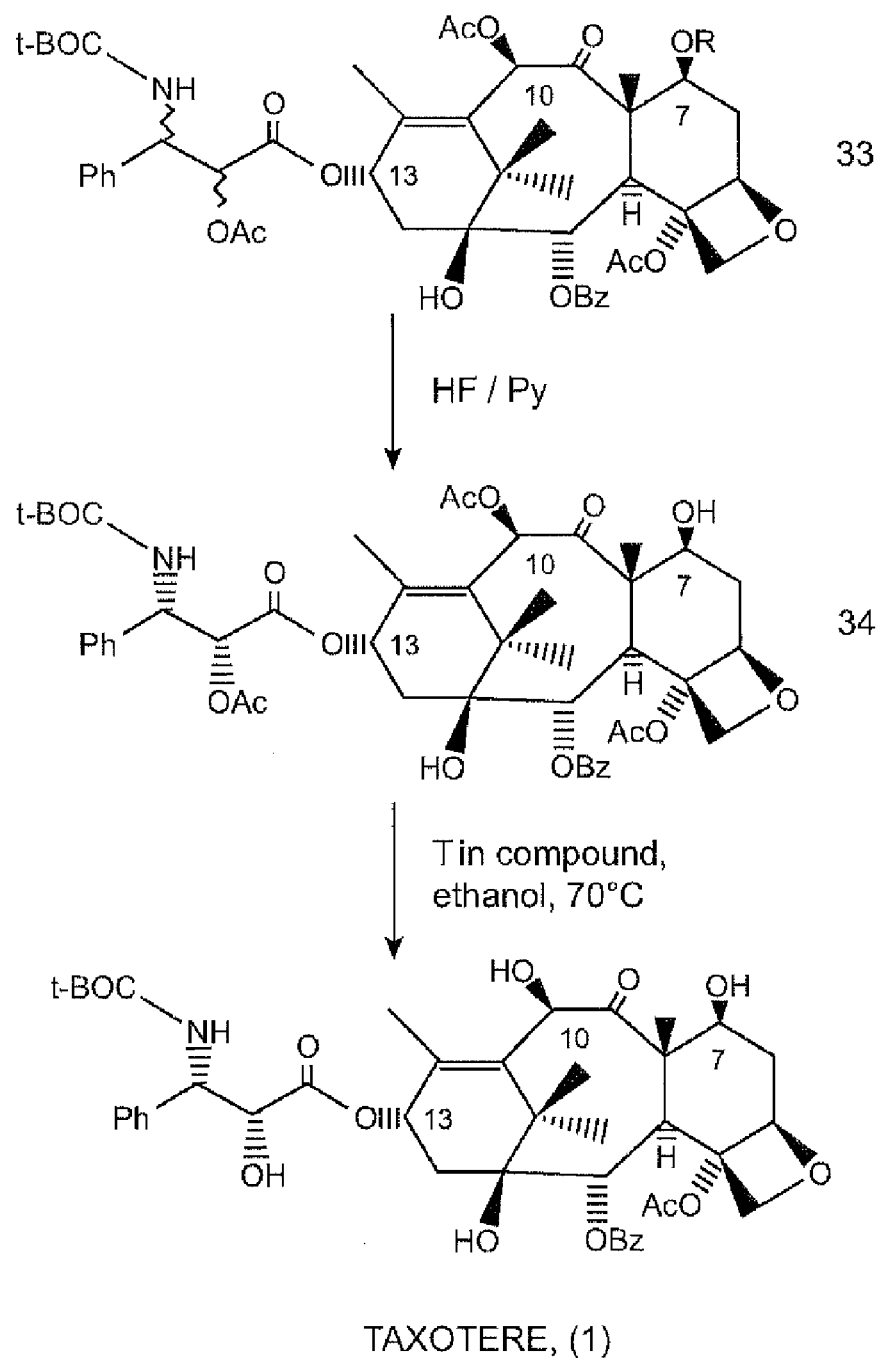
Figure 10:
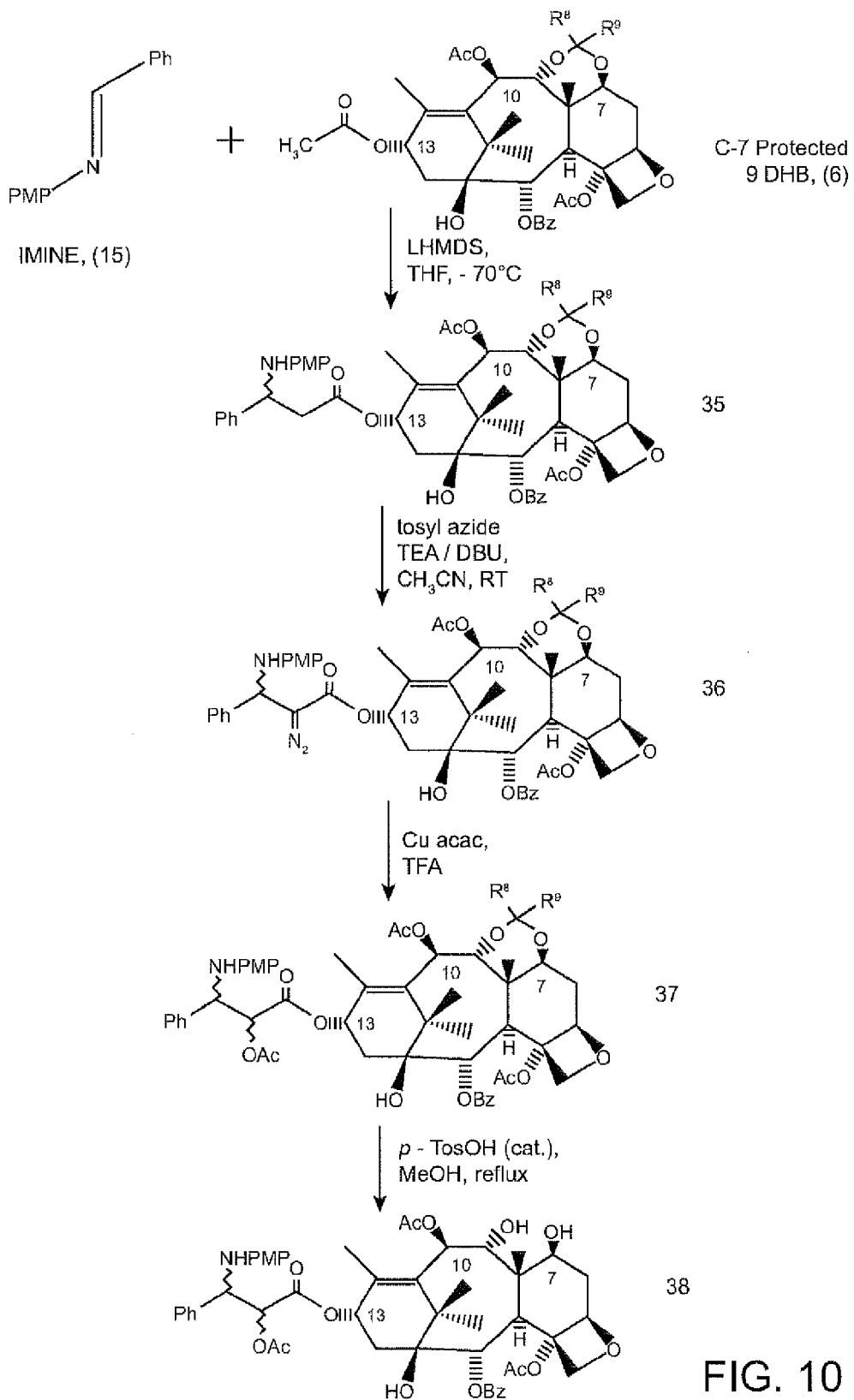
Figure 11:
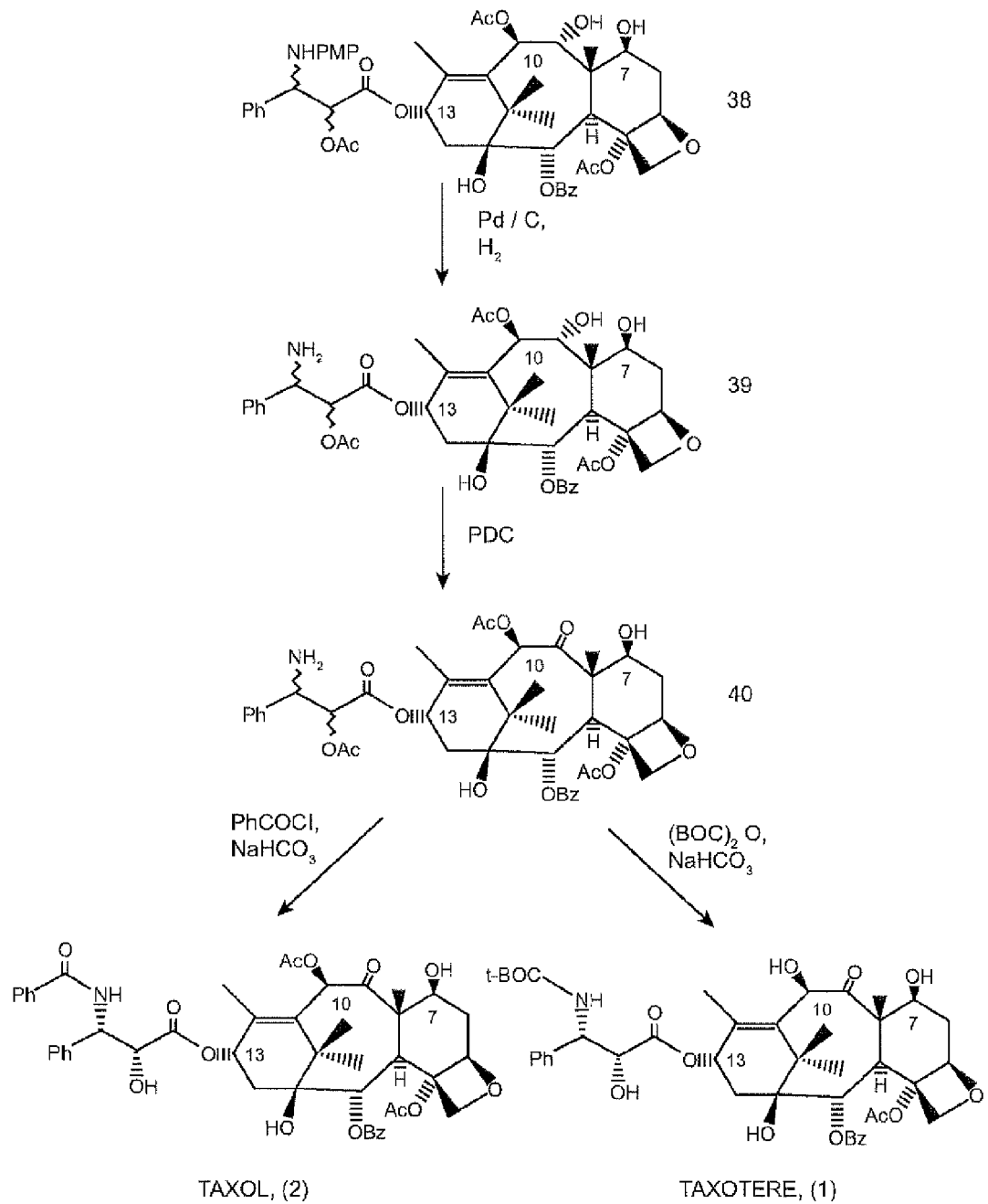
Figure 12:
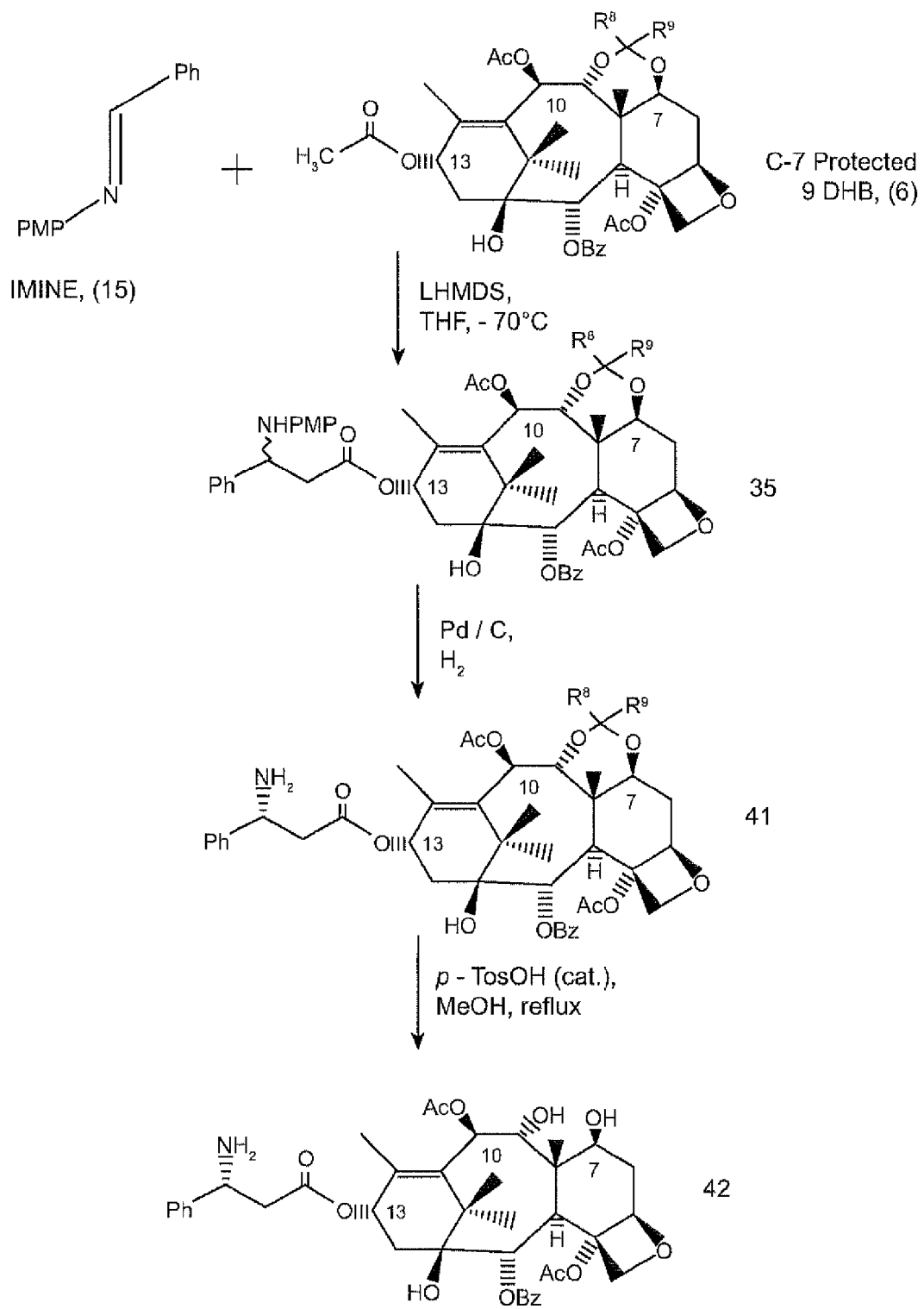
Figure 13:
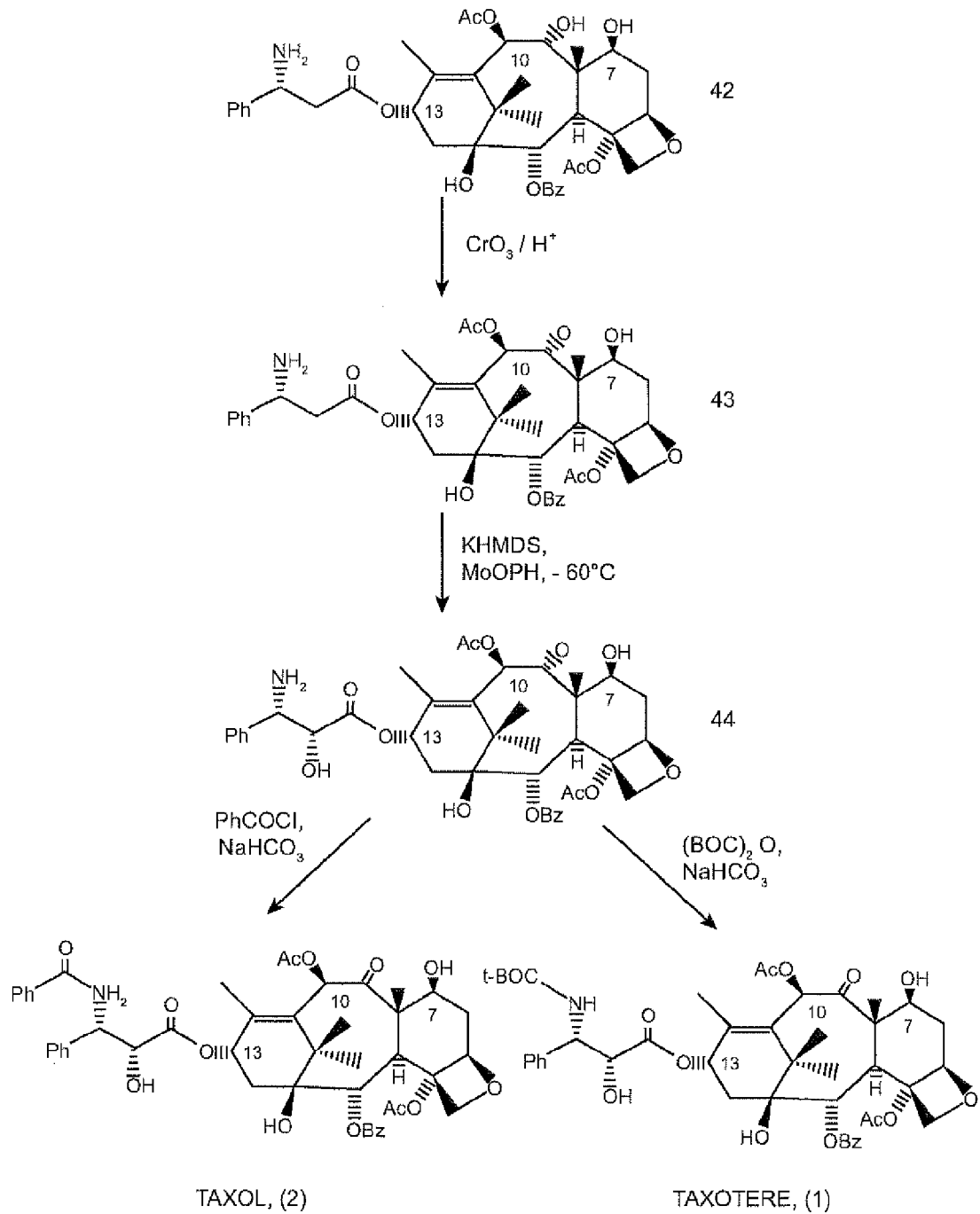
Figure 14:
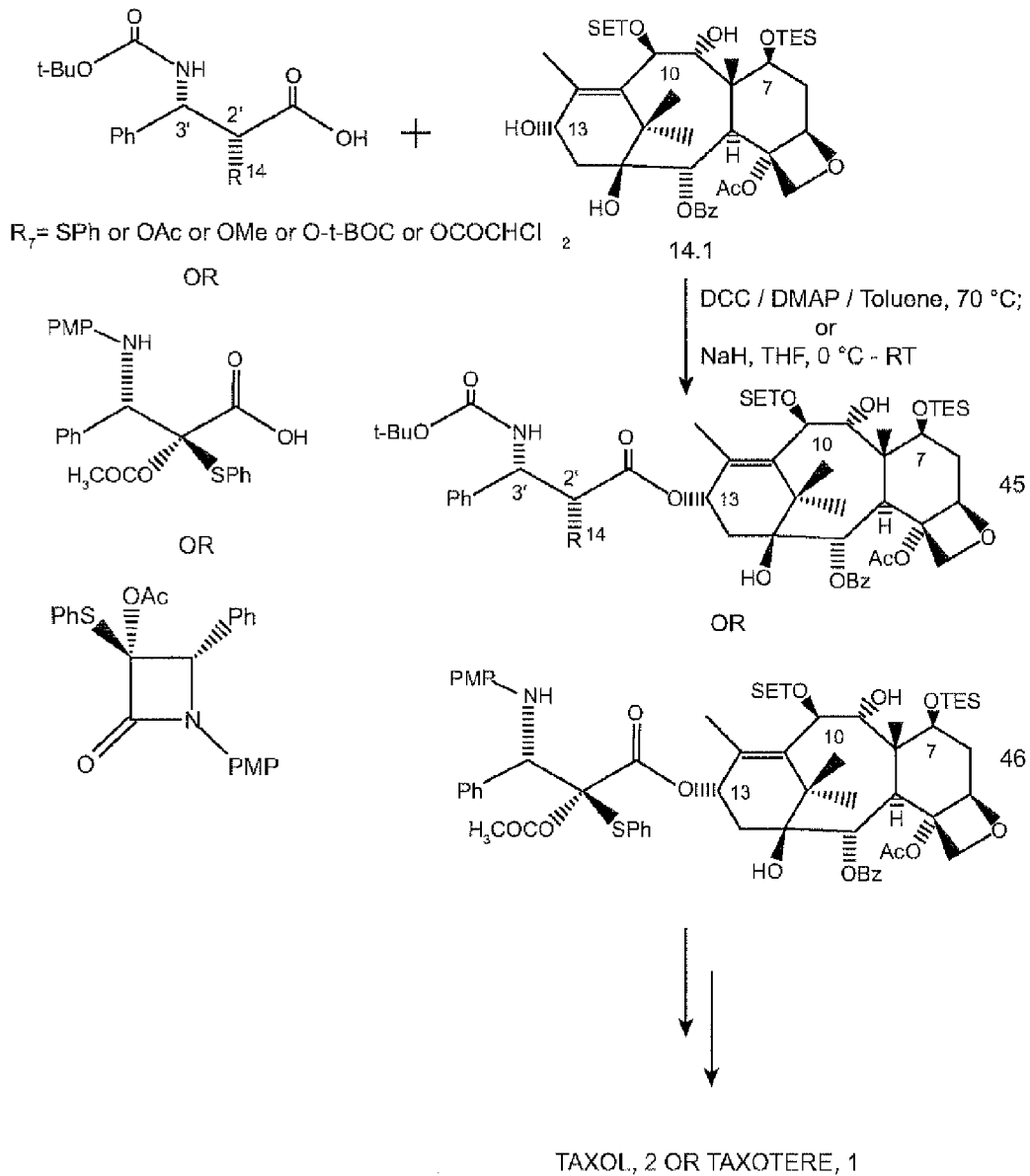
Figure 15:
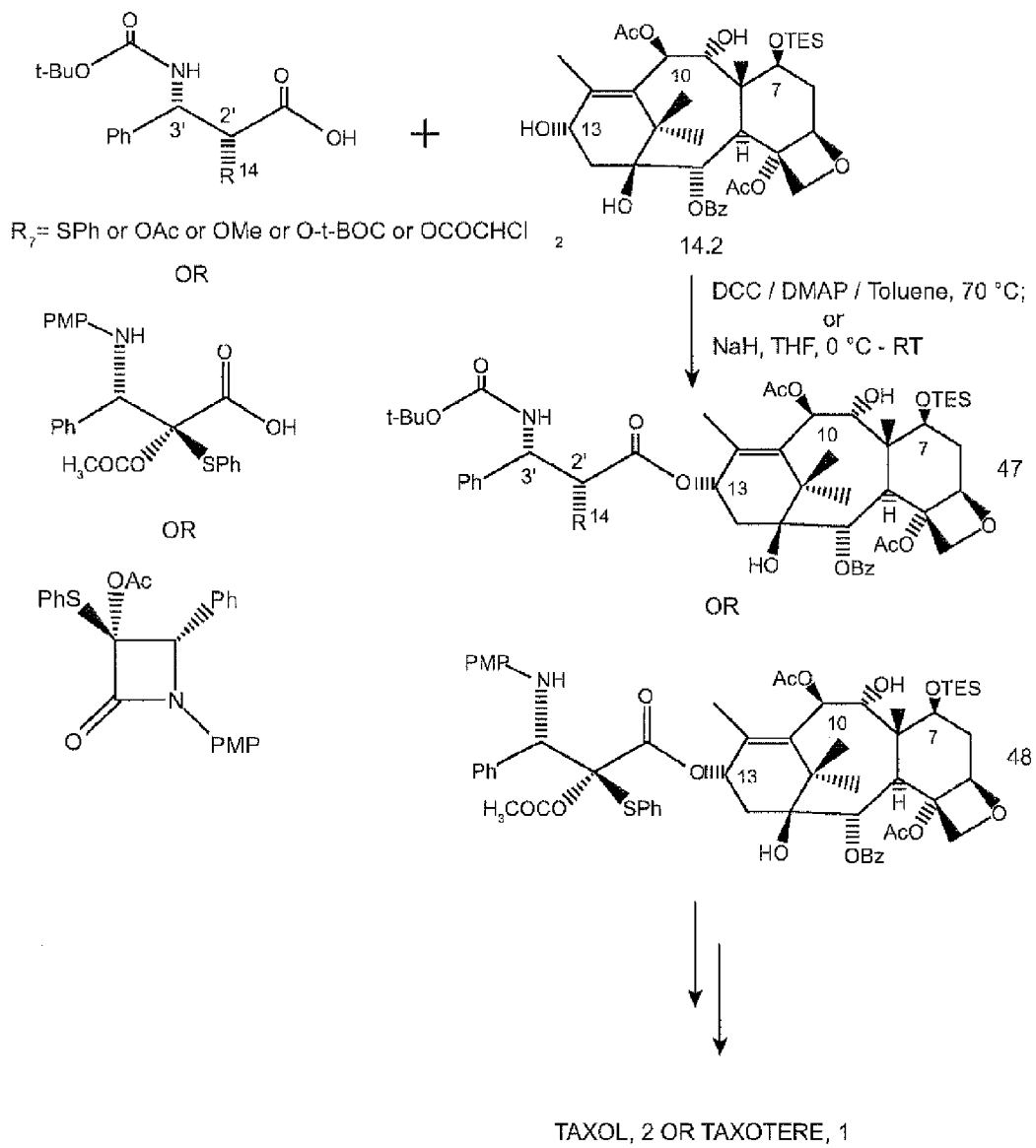

FIGS. 1, 2, 3, 3A, 4, 5, 6, 7, 8, 9, 10, 11, 12, 13, 14 and 15 illustrate chemical reactions according to the present invention.

DETAILED DESCRIPTION OF THE INVENTION

Before providing a detailed description of the present invention, the following terms are defined.

A. Definitions

The term "hydroxy-protecting group" refers to a readily cleavable group bonded to the oxygen of a hydroxyl (—OH) group. Examples of hydroxy protecting groups include, without limitation, acetyl (Ac), benzyl (PhCH2), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), trichloroacetyl (OCCCl₃), 2,2,2-trichloroethoxycarbonyl (Troc), benzyloxymethyl (BOM), tert-butyl (t-Bu), triethylsilyl (TES), trimethylsilyl (TMS), and triisopropylsilyl (TIPS). The related term "protected hydroxy group" refers to a hydroxy group that is bonded to a hydroxy-protecting group. General examples of protected hydroxy groups include, without limitation, —O-alkyl, —O-acyl, acetal, and —O-ethoxyethyl, where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloro ethoxycarbonyloxy, benzyloxycarbonyloxy, tert.-butoxycarbonyloxy, 1-cyclopropyl ethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, capryloyloxy, acryloyloxy, methylcarbamoyloxy, phenylcarbamoyloxy, naphthylcarbamoyloxy, and the like. Hydroxy protecting groups and protected hydroxy groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The term "thiol-protecting group" refers to a readily cleavable group bonded to the sulfur of a thiol (—SH) group. Examples of thiol protecting groups include, without limitation, triphenylmethyl (trityl, Trt), acetamidomethyl (Acm), benzamidomethyl, 1-ethoxyethyl, benzoyl, and the like. The related term "protected thiol group" refers to a thiol group that is bonded to a thiol-protecting group. General examples of protected thiol groups include, without limitation, —S-alkyl (alkylthio, e.g., $C_1$–$C_{10}$alkylthio), —S-acyl (acylthio), thioacetal, —S-aralkyl (aralkylthio, e.g., aryl ($C_1$–$C_4$)alkylthio), where some specific protected thiols groups include methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio, benzylthio, phenethylthio, propionylthio, n-butyrylthio and iso-butyrylthio. Thio protecting groups and protected thio groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The term "amine protecting group" refers to groups known in the art that can be used to protect an amine group from undergoing an undesired chemical reaction. Examples of amine protecting groups include, but are not limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structure of some protecting groups, as well as nomenclature used to identify those chemical structures.

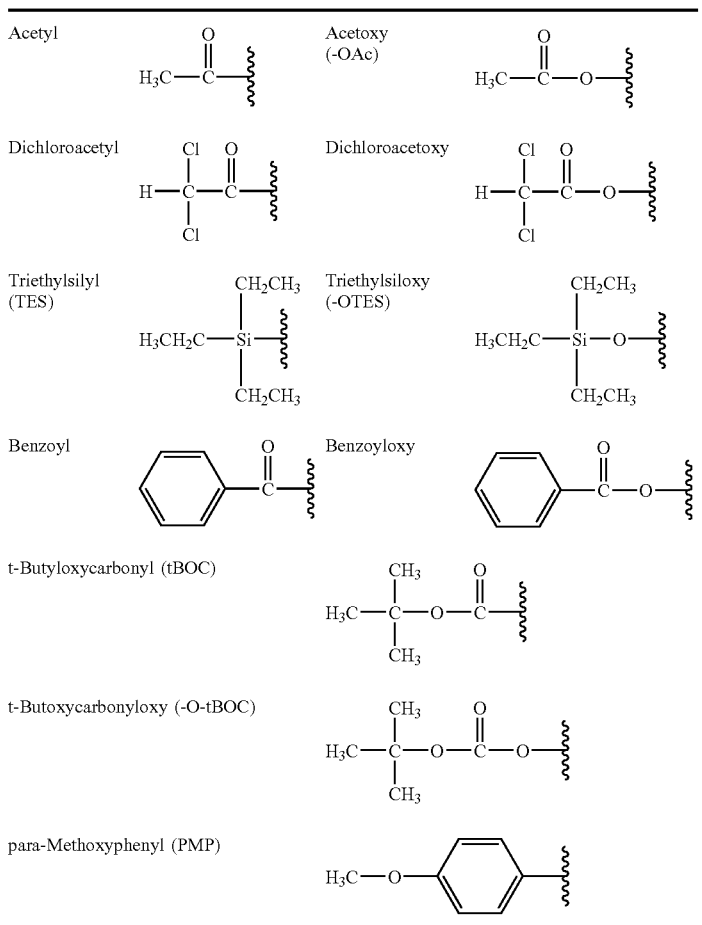

The term "alkyl" refers to a hydrocarbon structure wherein the carbons are arranged in a linear, branched, or cyclic manner, including combinations thereof. Lower alkyl refers to alkyl groups of from 1 to 5 carbon atoms. Examples of lower alkyl groups include methyl, ethyl, propyl, isopropyl, butyl, s- and t-butyl and the like. Preferred alkyl groups are those of C20 or below. More preferred alkyl groups are those of C13 or below. Cycloalkyl is a subset of alkyl and includes cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkenyl" refers to an alkyl group having at least one site of unsaturation, i.e., at least one double bond.

The term "alkynyl" refers to an alkyl group having at least one triple bond between adjacent carbon atoms.

The terms "alkoxy" and "alkoxyl" both refer to moieties of the formula —O-alkyl. Examples include methoxy, ethoxy, propoxy, isopropoxy, cyclopropyloxy, cyclohexyloxy and the like. Lower-alkoxy refers to groups containing one to four carbons. The analogous term "aryloxy" refers to moieties of the formula —O-aryl.

The term "acyl" refers to moieties of the formula —C(=O)-alkyl. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

The term aryl refers to phenyl or naphthyl. Substituted aryl refers to mono- and poly-substituted phenyl or naphthyl. Exemplary subsituents for aryl include one or more of halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

The term "heteroaryl" refers to a 5- or 6-membered heteroaromatic ring containing 1–3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0–3 heteroatoms selected from O, N, or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

The term "leaving group" (LG) refer to a chemical moiety that may be displaced during a substitution or elimination reaction. Exemplary leaving groups include halide (e.g., bromide and chloride) and as tosyl.

The term "brominating agent" refers to a chemical reactant that may be used to replace a hydroxyl group with a bromide. Exemplary brominating agents include, without limitation, thionyl bromide, phosphoryl bromide, a mixture of triphenylphosphine and carbon tetrabromide, N-bromosuccinimide (NBS), tetramethyl-2-fluoroformamidiniumbromide, tetraethyl-2-fluoroformamidinium-bromide, tetra-n-propyl-2-fluoroformamidiniumbromide, tetraisopropyl-2-fluoro-formamidiniumbromide, tetra-n-butyl-2-fluoro-formamidiniumbromide, tetra-n-pentyl-2-fluoroformamidiniumbromide, tetra-n-hexyl-2-fluoroformamidiniumbromide, 2-fluoro-1,3-dimethylimidazoliniumbromide, 2-fluoro-1,3-diethylimidazolinium-bromide, 2-fluoro-1,3-di-n-propylimidazoliniumbromide, 2-fluoro-1,3-di-n-butyl-imidazoliniumbromide, 2-fluoro-1,3-di-n-pentylimidazoliniumbromide, 2-fluoro-1,3-di-n-hexylimidazoliniumbromide, N,N-dimethyl-N',N'-dimethylphenylfluoroformamidiniumbromide, fluoro-bis(1-piperidyl)methyliumbromide, tetramethyl-2-chloroformamidiniumbromide, tetraethyl-2-chloroformamidiniumbromide, 2-chloro-1,3-dimethylimidazoliniumbromide and 2-chloro-1,3-diethylimidazoliniumbromide.

Many of the methods and compounds of the present invention derive from 9-dihydro-13-acetylbaccatin III (9-DHB). 9-DHB can be obtained by a number of different methods described by Gunawardana G. P. et al., *J. Nat. Prod.* 1992, 55, 1686 and U.S. Pat. No. 5,5530,020; Zamir et al., *Can. J. Chem.* 1995, 73, 655 and Jian Liu's U.S. Pat. No. 6,229,027. In one aspect, the present invention is directed towards providing a novel semi-synthetic route to produce taxane intermediates from naturally occurring 9-dihydro-13-acetylbaccatin III (9-DHB, 5) which is present in abundant quantities in *Taxus canadensis*. The intermediates can be used for the preparation of docetaxel or paclitaxel.

Compounds of the present invention contain the baccatin molecular framework, which is identified in a preferred stereochemical configuration as follows:

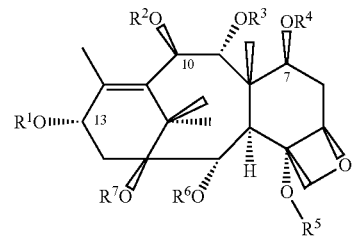

wherein each of $R^1$, $R^2$, $R^3$, $R^4$, $R^5$, $R^6$, and $R^7$ may be hydrogen or a hydroxyl protecting group as defined later herein. Two of $R^1$, $R^2$, $R^3$, $R^4$, $R^5$, $R^6$, and $R^7$ may be protected by a single protecting group. For example, the present invention provides compounds wherein $R^3$ and $R^4$ are linked together to provide a single protecting group for the C7 and C9 hydroxyl groups, as follows, where $R^8$ and $R^9$ are alkyl groups:

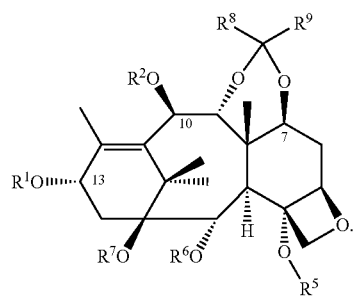

As another example, the present invention provides compounds wherein $R^2$ and $R^3$ are linked together to provide a protecting group for the C9 and C10 hydroxyl groups, as follows, where $R^{10}$ and $R^{11}$ are alkyl group:

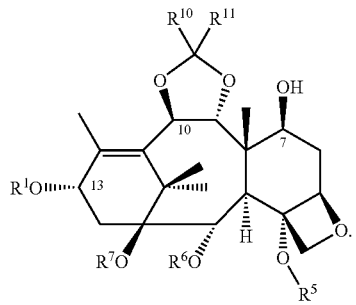

As described in more detail herein, taxol and derivatives thereof may be synthesized from 9-dihydro-13-acetylbaccatin III by a number of protection, oxidation, reduction, deprotection and addition of functional groups. For example, and as shown in Schemes 1–3, the C7 hydroxyl group of a C10 acylated taxane derivative can be selectively protected using any of a variety of hydroxyl protecting groups, such as acetal, ketal, silyl, and removable acyl protecting groups. For example, the C7 hydroxyl group may be silylated using any of a variety of common silylating agents including, but not limited to, tri(hydrocarbonyl)silyl halides and tri(hydrocarbonyl)silyl triflates. The hydrocarbonyl moieties of these compounds may be substituted or unsubstituted and preferably are substituted or unsubstituted alkyl or acyl. For example, the C7 hydroxyl group of 9-dihydro-13-acetylbaccatin III can be selectively silylated using silylating agents such as tribenzylsilyl chloride, trimethylsilyl chloride, triethylsilyl chloride, dimethylisopropylsilyl chloride, dimethylphenylsilyl chloride and the like. Alternatively, selective acylation of the C7 hydroxyl group of a C10 acylated taxane can be achieved using any of a variety of common acylating agent, but not limited to substituted and unsubstituted carboxylic acid derivatives, e.g., carboxylic acid halides, anhydrides, dicarbonates, isocyanates and haloformates. For example, the C7 hydroxyl group of 9-dihydro-13-acetylbaccatin III can be selectively acylated with dibenzyl dicarbonate, diallyl dicarbonate, 2,2,2-trichloroethyl chloroformate, benzyl chloroformate or dichloroacetyl chloride or another common acylating agent. These acylating reactions may optionally be carried out in the presences or absences of an amine base.

The present invention is generally directed to baccatin compounds. In one aspect, the baccatin compounds have the following basic structure, with the R groups being variously defined herein.

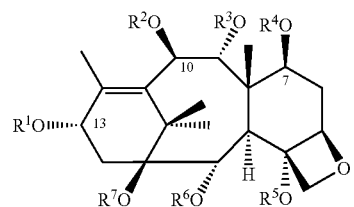

A preferred taxane intermediate of the present invention is represented by the general formula (III)

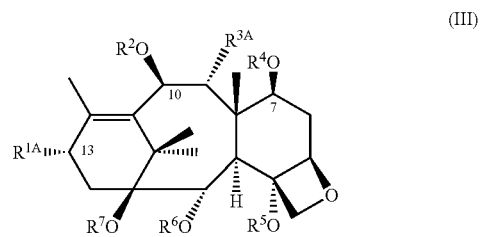

wherein $R^{1A}$ is represented by the following structure, where PG is an amine protecting group,

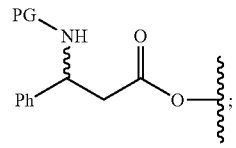

$R^2$ is acetyl; $R^{3A}$ is selected from azide, bromo, fluoro, amine and carbonyl groups; $R^4$ is selected from ethers, esters, carbonates and silyl groups, and $R^5$, $R^6$ and $R^7$ are independently selected from hydrogen and hydroxyl protecting groups, where in a preferred embodiment $R^5$ is acetyl, $R^6$ is benzoyl and $R^7$ is hydrogen. Certain compounds within the scope of this general formula are described in Schemes 4–15 as discussed below. Methods to prepare the precursor baccatin III compound are provided in Schemes 1–3A. The precursor baccatin III compound, in a protected form, may be reacted with an imine in the presence of an alkali metal or alkaline earth metal alkoxide of the protected baccatin III at the C13 ester functionality. The enolate can readily be generated by reacting the protected baccatin III with an alkali metal or alkaline earth metal base such as sodium hexamethyldisilazide, potassium hexamethyldisilazide, lithium hexamethyl-disilazide, sodium diisopropylamide, potassium diisopropylamide, lithium diisopropylamide, sodium hydride, potassium hydride, lithium hydride, calcium hydride, magnesium hydride, in a dry nonprotic organic solvent such as tetrahydrofuran (THF), dioxane, ether, dimethoxyethane (DME), diglyme, dimethylformamide (DMF), mixtures of these solvents with hexane, toluene, and xylene, in a preferred temperature range at about −100° C. to about 50° C., more preferably at about −78° C. to about 25° C. This reaction is preferably carried out under inert atmosphere such as nitrogen or argon.

In addition, the present invention is directed to a process for the preparation of taxol, taxotere, baccatin III or 10-deacetylbaccatin III from 9-dihydro-13-acetylbaccatin III in which the C9 hydroxy substituent may thereafter be selectively replaced by other functional groups and oxidized to the C9 keto substituent or protected C7, C9 group according to the formula I and II.

(I)

(II)

In one aspect, the preparation of these taxane intermediates of formula I and II comprises the steps of: (i) protecting a hydroxyl group at C7 and C9 positions and (ii) oxidation at C9 position. More details about the reactions mentioned above, and additional reactions and compounds of the present invention, are discussed below in connection with Schemes 1–15.

Scheme 1

As shown in Scheme 1, the hydroxyl group at the 7 position of 9-DHB may be converted to a protected form, i.e., a protected hydroxyl group, as present in compound 6. The C7 hydroxyl group of a C10 acylated taxane derivative can be selectively protected using any of a variety of hydroxyl protecting groups, such as acetal, ketal, silyl, and removable acyl protecting groups. For example, the C7 hydroxyl group may be silylated using any of a variety of common silylating agents including, but not limited to, tri(hydrocarbonyl)silyl halides and tri(hydrocarbonyl)silyl triflates. The hydrocarbonyl moieties of these compounds may be substituted or unsubstituted and preferably are substituted or unsubstituted alkyl or acyl. For example, the C7 hydroxyl group of 9-dihydro-13-acetylbaccatin III can be selectively silylated using silylating agents such as tribenzylsilyl chloride, trimethylsilyl chloride, triethylsilyl chloride, dimethylisopropylsilyl chloride, dimethylphenylsilyl chloride and the like. Alternatively, selective acylation of the C7 hydroxyl group of a C10 acylated taxane can be achieved using any of a variety of common acylating agent, but not limited to substituted and unsubstituted carboxylic acid derivatives, e.g., carboxylic acid halides, anhydrides, dicarbonates, isocyanates and haloformates. For example, the C7 hydroxyl group of 9-dihydro-13-acetylbaccatin III can be selectively acylated with dibenzyl dicarbonate, diallyl dicarbonate, 2,2,2-trichloroethyl chloroformate, benzyl chloroformate or dichloroacetyl chloride or another common acylating agent. These acylating reactions may optionally be carried out in the presences or absences of an amine base.

Scheme 1 provides Reaction 1 summarized below.

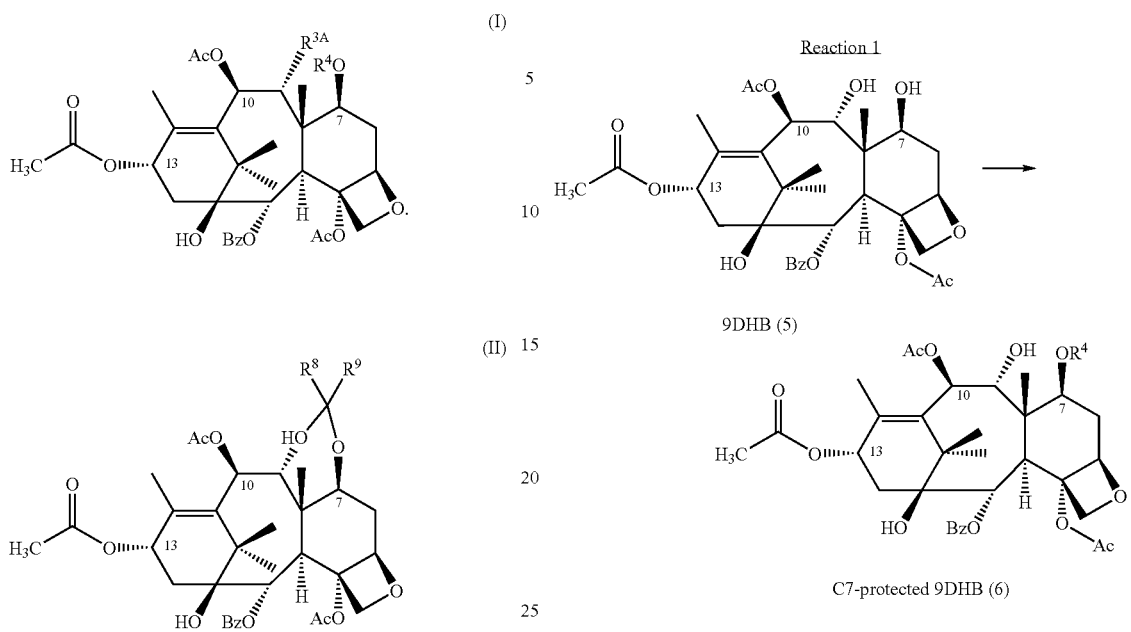

Exemplary reaction conditions to achieve Reaction 1 are as follows: 9DHB is dissolved in anhydrous DCM (dichloromethane) or THF (tetrahydrofuran) under an argon atmosphere at room temperature. To this solution is added DMAP (dimethylaminopyridine) followed by dichloroacetyl chloride or triethyl silyl chloride or any other chloride containing the respective protecting groups. The mixture is left at room temperature for overnight. The mixture is then quenched with cold water and extracted thrice with DCM. The organic layer is washed with water and than with brine to remove unwanted salts. The organic layer may then be dried and evaporated under vacuum, and the residue recrystallized or column chromatographed with DCM/EtOAc mixtures to afford C7 protected 9 DHB as a white solid.

Thereafter, the hydroxyl group at the 9 position of compound 6 may be converted to an azide group, to provide compound 7. Compound 7 may be oxidized to provide compound 8 having a carbonyl group at the 9 position. Hydrolysis of compound 8 affords compound 9, which can be elaborated according to known methodology to either the C7-protected version of 10DAB, or to the C7-protected version of BACC III.

The conversion of compound 6 to the corresponding azide 7 may be accomplished with baccatin III compounds having the set of hydroxyl protecting groups shown in Scheme 1, or with any other set of hydroxyl protecting groups. Thus, the present invention generally provides a method comprising reacting a compound of the formula

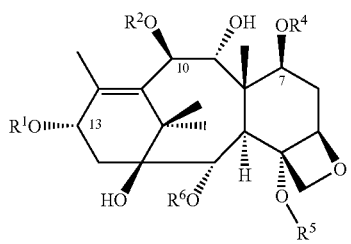

with an azide compound most preferably diphenylphosphoryl azide in an organic base such as 1,8-diazabicyclo[5.4.0]undec-7-ene (DBU), so as to provide a compound of the following formula

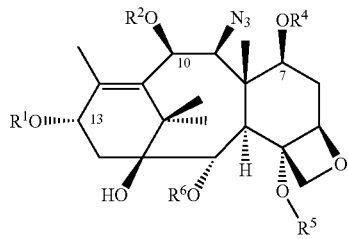

wherein $R^1$, $R^2$, $R^4$, $R^5$ and $R^6$ each represent hydrogen or a hydroxyl protecting group, independently selected at each location. In addition, the present invention provides the product of this azide formation reaction, namely a compound of the formula

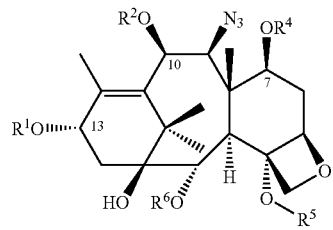

wherein $R^1$, $R^2$, $R^4$, $R^5$ and $R^6$ each represent hydrogen or a hydroxyl protecting group, independently selected at each location.

The conversion of compound 6 to compound 7 is shown in Reaction 2.

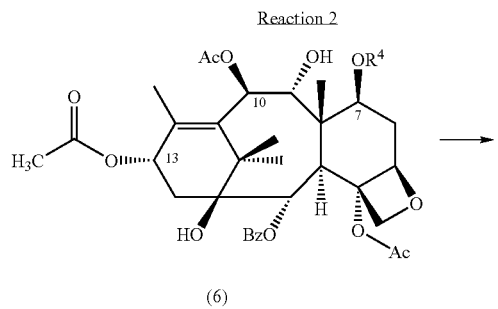

Exemplary reaction conditions to achieve Reaction 2 are as follows: C7 protected 9 DHB is dissolved in THF and diphenylphosphoryl azide added under an argon atmosphere. The mixture is cooled to 0° C. and DBU (1,8diazabicyclo[5.4.0]undec-7-ene) added dropwise. (caution: the DBU addition causes an exotherm. The reaction temperature is maintained below 5° C. by carefully controlling the rate of addition). A thick white precipitate forms during the DBU addition. The reaction is stirred at 1° C. for 1 hr, and then it is warmed to room temperature and stirred under argon for 24 hrs. The resulting homogenous reaction is diluted with methyl tert-butyl ether (MTBE) and water is added. After the water layer is removed, the organic phase is washed with water and 0.5M citric acid monohydrate. The organic layer is dried and concentrated under reduced pressure. The product is purified by column chromatography using mixtures of DCM/EtOAc and finally crystallized from DCM/hexane to give the pure product.

The conversion of compound 7 to the corresponding ketone 8 is illustrated in Reaction 3.

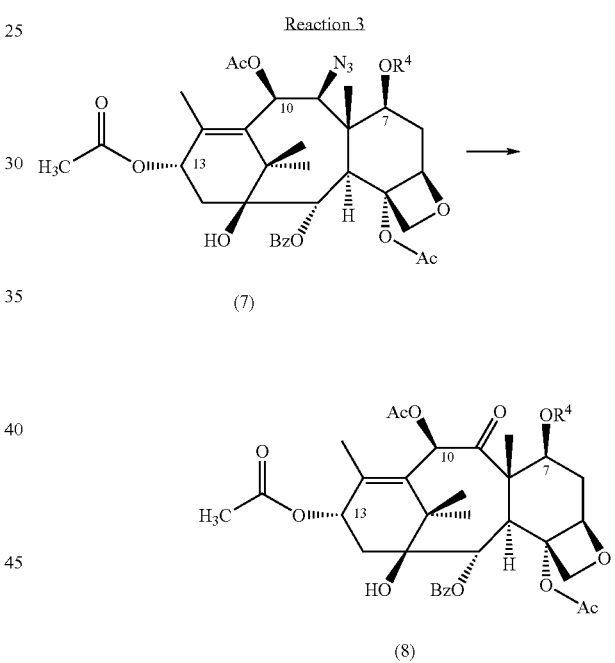

Exemplary reaction conditions to achieve Reaction 3 are as follows: Ethanol is added to n-butyllithium (1.6M) in hexane. The mixture is dissolved in anhydrous THF and stirred at 25° C. The azide compound 7 from reaction 1 in THF is added dropwise, nitrogen gas is evolved and after 30 min at 25° C. the reaction is quenched with 3N HCl. The solution is extracted with two portions of ether. The combined organic layer were dried and concentrated in vacuo. The crude mixture was purified by column chromatography and crystallized to afford the pure compound 8. (Note: This hydrolysis may also give deprotection at of the acetate group at C-13 position, thus giving C7 protected baccatin III). The conversion of compound 7 to the corresponding ketone 8 may be accomplished with baccatin III compounds having the set of hydroxyl protecting groups shown in Scheme 1 (Reaction 3), or with any other set of hydroxyl protecting groups.

The compound 8 may be converted to compound 9 as shown in Scheme 1 and Reaction 4.

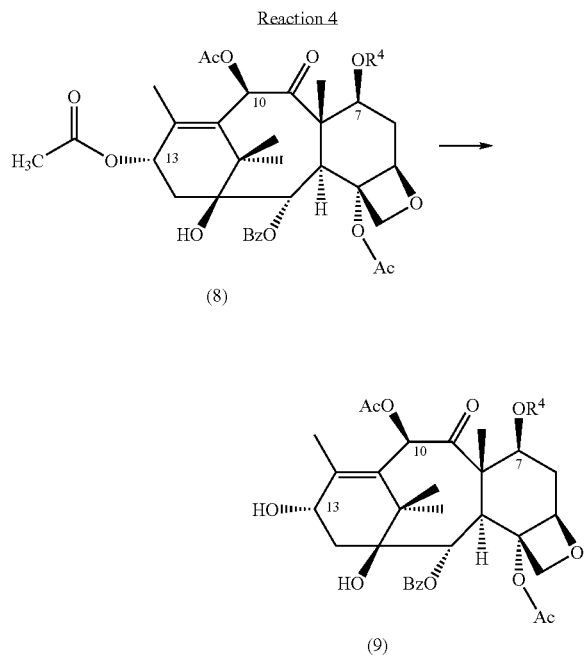

Exemplary reaction conditions to achieve the conversion shown in Reaction 4 are as follows: Compound 8 is hydrolyzed using a base in one aspect, and a reducing salt in another aspect. Suitable bases include sodium carbonate, sodium bicarbonate, butyl lithium and methyl lithium. The term "reducing salt" refers to a reducing agent in the presence of a Lewis acid. Suitable reducing agents include tetrabutylammonium borohydride, lithium borohydride, sodium triacetoxy borohydride and sodium borohydride. Suitable Lewis acids include $SbCl_5$, $ZnCl_2$, $CuCl_2$, $PbCl_2$, $GeCl_2$, $SnBr_2$, $SnI_2$ and $CoBr_2$. For example, compound 8 is dissolved in DCM and a minimum volume of water added. To this mixture, solid $NaBH_4$ is added in small portions with vigorous stirring and a catalytic amount of $ZnCl_2$ (a Lewis acid) is added. After completion of the addition, the reaction mixture is stirred for an additional 15 min, then $NH_4Cl$ is added as a concentrated aqueous solution, the layers are separated and the aqueous phase is extracted with DCM. The combined organic extract is dried and evaporated to give the crude product. Purification by dry-flash chromatography using DCM/MeOH (95/5) affords the pure hydrolysed product.

Thus, the present invention generally provides a method comprising reacting a compound of the formula

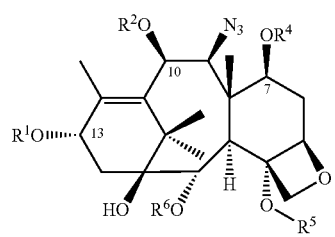

to provide a compound of the formula

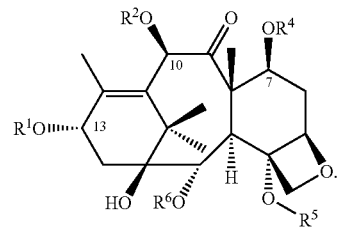

wherein $R^1$, $R^2$ $R^4$, $R^5$ and $R^6$ each represent a hydroxyl protecting group, independently selected at each location.

Scheme 2

In additional aspects, the present invention provides reactions as set forth in Scheme 2. For example, the invention provides for the deprotection of the C13 hydroxyl group of 9-DHB (compound 5) to provide the corresponding alcohol 5.1. In a separate aspect, compound 5.1 may be subjected to selective oxidation of the C9 hydroxyl group to provide Bacc III (compound 4). The C10 hydroxyl group of compound 4 may optionally be deprotected to provide 10DAB, i.e., compound 3. In another aspect, the C9 hydroxyl group of 9-DHB may be selectively oxidized to the corresponding carbonyl group, to provide compound 11. Alternatively, the C9 hydroxyl group of 9-DHB may be converted to a bromide to provide compound 10, and then compound 10 subjected to a selective oxidation to provide a carbonyl group at C10, as in compound 11. The C13 hydroxyl group of compound 11 may then be deprotected to provide Bacc III (compound 4). The C10 hydroxyl group of compound 4 may optionally be deprotected to provide 10DAB, i.e., compound 3.

Thus, in one aspect of the present invention, there is provided a method to prepare a taxane comprising the steps of bromination at C-7 or C-9 position with a suitable brominating agent followed by oxidation at the C-9 position with a suitable oxidizing agent. For example, the C9 hydroxyl group of 9-DHB may be substituted with a halide, e.g., bromide, to provide compound 10. In a separate aspect, compound 10, or the chloro or iodo analog, may be oxidized to the corresponding carbonyl compound 11. As stated above, compound 11 may be converted to compound 3 or 4.

Compound 5 has a certain set of hydroxyl protecting groups (e.g., an acetate at C10). However, the conversion of the hydroxyl at C9 or C7 to a halide is not dependent on the choice of those hydroxyl protecting groups, and in general the halogenation reaction may be accomplished with other protected baccatin molecules. In general, the present invention provides a method for brominating a compound of the formula

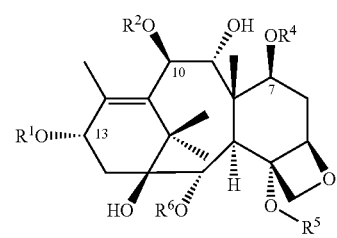

to provide a compound of the formula

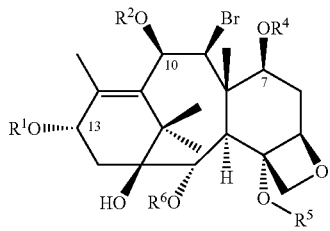

wherein $R^1$, $R^2$, $R^4$, $R^5$ and $R^6$ each represent hydrogen or a hydroxyl protecting group, independently selected at each location.

For example, compound 5 may be dissolved in anhydrous DCM under an argon atmosphere and cooled to −20° C. Any brominating agent (such as acetyl bromide, HBr or NBS etc) may be used. The brominating agent is added dropwise to the stirred solution at this temperature and left to react for several hours. When all the starting material is consumed as evidenced by TLC, the reaction is stopped and worked up as usual. The crude product is purified by column chromatography using mixtures of ethyl acetate and DCM to afford the pure compound 10.

The resulting halogen-containing compound is also an aspect of the present invention. Thus, in one aspect the invention provides a compound of the formula

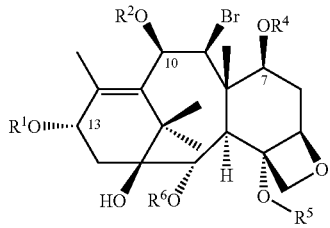

wherein $R^1$, $R^2$ $R^4$, $R^5$ and $R^6$ each represent hydrogen or a hydroxyl protecting group, independently selected at each location. In a preferred embodiment, $R^1$ is acetyl, $R^2$ is acetyl, $R^4$ is dichloroacetyl or acetyl, $R^5$ is acetyl, and $R^6$ is benzoyl as in compound 5. The invention also provides the corresponding chloride and iodide analogs, which may be prepared from a chlorinating agent and an iodination reagent, respectively, acting upon compound 5 or an analog thereof having different hydroxyl protecting groups.

In addition, the present invention generally provides a method comprising oxidation of a compound such a compound 10, but more generally a compound of the formula

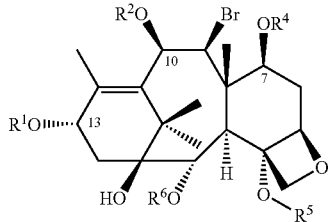

to provide a compound of the formula

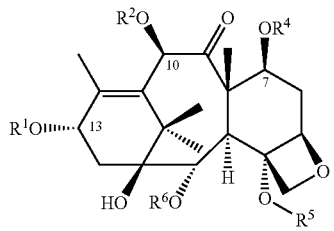

wherein $R^1$, $R^2$, $R^4$, $R^5$ and $R^6$ each represent hydrogen or a hydroxyl protecting group, independently selected at each location.

As mentioned above, the present invention provides a process comprising bromination of a compound of the formula

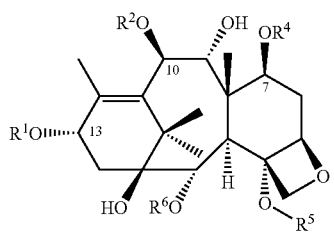

to provide a compound of the formula

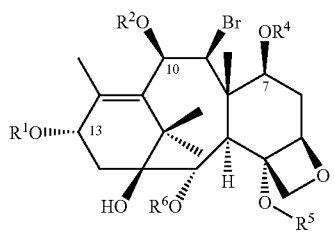

wherein $R^1$, $R^2$, $R^4$, $R^5$ and $R^6$ each represent hydrogen or a hydroxyl protecting group, independently selected at each location. In one embodiment, this process results in an admixture of the stated brominated product and the corresponding carbonyl compound. Thus, in one aspect, the process of forming a compound of the formula

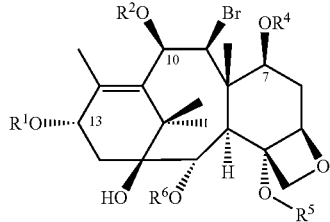

provides this compound in admixture with a compound of formula

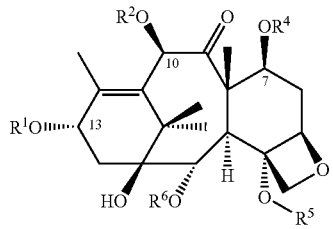

wherein $R^1$, $R^2$, $R^4$, $R^5$ and $R^6$ each represent hydrogen or a hydroxyl protecting group, independently selected at each location.

The conversion of compound 11, or more generally a compound of the formula

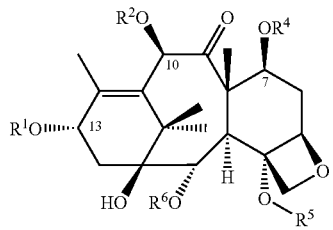

wherein $R^1$ is a hydroxyl protecting group and $R^2$, $R^4$, $R^5$ and $R^6$ each represent hydrogen or a hydroxyl protecting group, independently selected at each location, to the corresponding compound wherein $R^1$ is hydrogen, as illustrated by the hydrolysis reaction in Scheme 2, is another aspect of the present invention. In one aspect, the removal of the protecting group at C13 is accomplished by base, while in another aspect the removal of the protecting group is accomplished using a reducing salt. Suitable bases include sodium carbonate, sodium bicarbonate, butyl lithium and methyl lithium. The term "reducing salt" refers to a reducing agent in the presence of a Lewis acid. Suitable reducing agents include tetrabutylammonium borohydride, lithium borohydride, sodium triacetoxy borohydride and sodium borohydride. Suitable Lewis acids include $SbCl_5$, $ZnCl_2$, $CuCl_2$, $PbCl_2$, $GeCl_2$, $SnBr_2$, $SnI_2$ and $CoBr_2$. For example, compound 11 is dissolved in DCM and a minimum volume of water added. To this mixture, solid $NaBH_4$ is added in small portions with vigorous stirring and a catalytic amount of $ZnCl_2$ (a Lewis acid) is added. After completion of the addition, the reaction mixture is stirred for an additional 15 min, then $NH_4Cl$ is added as a concentrated aqueous solution, the layers are separated and the aqueous phase is extracted with DCM. The combined organic extract is dried and evaporated to give the crude product. Purification by dry-flash chromatography using DCM/MeOH (95/5) affords the pure hydrolysed product.

Schemes 3 and 3a

The present invention provides additional reactions and intermediates that may be used to, for example, prepare 10 DAB (compound 3) and/or BACC III (compound 4). 9-DHB may be used as a starting material, as shown in Schemes 3 and 3a.

As shown in Scheme 3, 9-DHB may be converted to the corresponding ketal, e.g., an acetonide as shown in compound 12. For example, to a suspension of 9-DHB in acetone and dimethoxypropane at ca. 25° C. is added camphorsulfonic acid (CSA) and the mixture is stirred under an inert atmosphere for a couple of hours. The product mixture is quenched with saturated sodium bicarbonate, followed by extraction with ethyl acetate, then washing with brine and removal of solvent in vacuo to provide a residue that is purified by chromatography (e.g., dichloromethane/methanol mixtures) to provide a purified product.

In a separate aspect, the protecting group of the C13 hydroxyl of compound 12 may be removed to provide compound 13. For example, compound 12 may be dissolved in THF followed by the addition of a base, e.g., sodium carbonate, sodium hydrogen carbonate and hydrogen peroxide, sequentially with vigorous stirring. After completion of the reaction as seen by the TLC, the reaction mixture is worked up as usual. Purification by dry-flash chromatography using DCM/MeOH (95/5) afforde the pure hydrolysed product 13.

In a separate aspect, the acetonide group of compound 13 may be removed to provide compound 14. For example, compound 13 may be dissolved in THF followed by the addition of a base, e.g., sodium carbonate, sodium hydrogen carbonate and hydrogen peroxide, sequentially with vigorous stirring. After completion of the reaction as seen by the TLC, the reaction mixture is worked up as usual. Purification by dry-flash chromatography using DCM/MeOH (95/5) afforde the pure hydrolysed product 14.

In another aspect, as also shown in Scheme 3, the present invention provides a more direct route to compound 14, whereby compound 5 is treated with base, e.g., a mixture containing sodium carbonate, sodium bicarbonate and hydrogen peroxide, to remove the protecting groups at positions 10 and 13, and thereby provide compound 14. In yet another aspect, as shown in Scheme 3a, compound 5 may be exposed to hydrolysis conditions to provide compound 14a. The conversion of compound 5 to compound 14 (Scheme 3) removes hydroxyl protecting groups at each of C10 and C13, while the conversion of compound 5 to compound 14a (Scheme 3a) removes the hydroxyl protecting group at C10 while retaining the hydroxyl protecting group at C13. For example, compound 5 may be dissolved in THF followed by the addition of a base, e.g., sodium carbonate, sodium hydrogen carbonate and hydrogen peroxide, sequentially with vigorous stirring. After completion of the reaction as seen by the TLC, the reaction mixture is worked up as usual. Purification by dry-flash chromatography using DCM/MeOH (95/5) afforde the pure hydrolysed products, 14 and 14a.

As shown in Scheme 3, selective protection of the C7 hydroxyl group of compound 14 affords compound 14.2. The hydroxyl group at C9 of compound 14.2 may be oxidized to provide compound 14.4 (not shown), where removal of the hydroxyl protecting group at C7 of compound 14.4 provides BACC III (compound 4). The C10 protecting group in compound 4 may be removed to provide 10-DAB, i.e., compound 3. For example, 14 may be dissolved in anhydrous dichloromethane under an argon atmosphere at room temperature. To this solution is added pyridine followed by one equivalent of triethylsilyl chloride. The mixture is left at room temperature for overnight. Then one equivalent of triethylsily chloride or dichloroacetyl choride is added and again the mixture is left at room temperature overnight. The mixture is then quenched with cold water and extracted thrice with dichloromethane. The organic layer is washed with water and than with brine to remove unwanted salts. The organic layer may then be dried and evaporated under vacuum, and the residue recrystallized or column chromatographed with dichloromethane/ethyl acetate mixtures to afford the desired product 14.2.

In another aspect, when the desired target is compound 3, it may be prepared directly from compound 14 via compound 14.1, where compound 14.1 is prepared by protection of the C7 and C10 hydroxyl groups of compound 14. Oxidation of the C9 hydroxyl group of compound 14.1, followed by removal of the protecting groups at C7 and C10, affords 10-DAB (compound 3). For example, 14 may be dissolved in anhydrous dichloromethane under an argon atmosphere at room temperature. To this solution is added pyridine followed by two equivalents of triethylsilyl chloride or two equivalents of dichloroacetyl chloride. The mixture is left at room temperature for overnight. The mixture is then quenched with cold water and extracted thrice with dichloromethane. The organic layer is washed with water and than with brine to remove unwanted salts. The organic layer may then be dried and evaporated under vacuum, and the residue recrystallized or column chromatographed with dichloromethane/ethyl acetate mixtures to afford the desired product 14.1.

In another aspect, the C9 and C10 hydroxyl groups of compound 14 may simultaneously be protected by converting these groups to the corresponding ketal, e.g., an acetonide, which is illustrated by compound 14.3 as shown in Scheme 3. The analogous reaction may be conducted on a baccatin molecule having a hydroxyl protecting group at C13, e.g., compound 14a may be converted to the acetonide compound 14b as shown in Scheme 3a, using reaction conditions analogous to those described above.

Compound 14 is an aspect of the invention. Thus, the present invention provides a compound of the formula

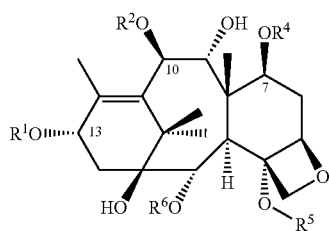

wherein $R^1$ is hydrogen, $R^2$ is hydrogen, $R^4$ is hydrogen, $R^5$ is acetyl, and $R^6$ is benzoyl.

Compound 14.1 is an aspect of the invention. Thus, the present invention provides a compound of the formula

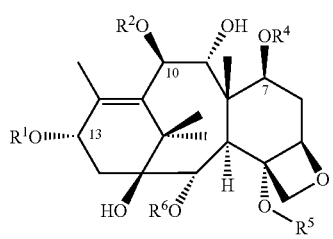

wherein $R^1$ is hydrogen, $R^2$ is TES or dichloroacetyl, $R^4$ is TES or dichloroacetyl, $R^5$ is acetyl, and $R^6$ is benzoyl.

Compound 14.2 is an aspect of the invention. Thus, the present invention provides a compound of the formula

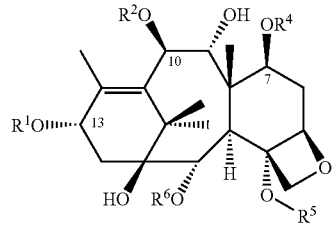

wherein $R^1$ is hydrogen, $R^2$ is acetyl, $R^4$ is TES or dichloroacetyl, $R^5$ is acetyl, and $R^6$ is benzoyl.

Compound 14.3 is a further aspect of the present invention. Thus, the present invention provides a compound of the formula

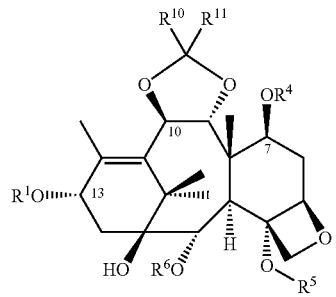

wherein $R^1$ is hydrogen, $R^4$ is hydrogen or TES or dichloroacetyl, $R^5$ is acetyl, $R^6$ is benzoyl, and $R^{10}$ and $R^{11}$ are independently selected from $C_1$–$C_6$ alkyl, e.g., methyl.

Compound 14a is also an aspect of the invention. Thus, the present invention provides a compound of the formula

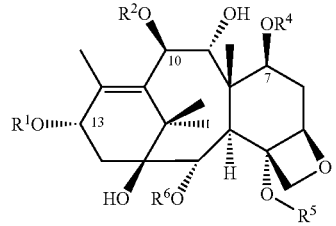

wherein $R^1$ is acetyl, $R^2$ is hydrogen, $R^4$ is hydrogen, $R^5$ is acetyl and $R^6$ is benzoyl.

Compound 14b is a further aspect of the present invention. Thus, the present invention provides a compound of the formula

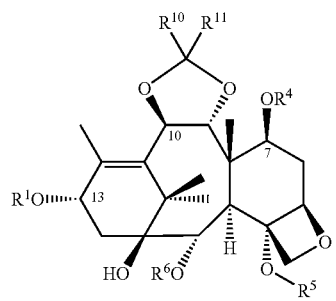

wherein $R^1$ is acetyl, $R^4$ is a hydroxyl protecting group, $R^5$ is acetyl, $R^6$ is benzoyl, and $R^{10}$ and $R^{11}$ are independently selected from $C_1$–$C_6$ alkyl, e.g., methyl.

Schemes 4–13

In general, Schemes 4–13 teach synthetic methodology which may be used to convert 9-DHB to taxol (compound 2) or taxotere (compound 1). As mentioned previously, 9-DHB is readily available from the Canadian Yew (*Taxus Canadensis*), and taxol and taxotere are both extremely valuable therapeutic agents. Thus, in various aspects, the present invention provides the synthetic methodology shown in Schemes 4–13, where each of the individual reaction steps shown in the Schemes is a separate aspect of the invention, where every two sequential reaction steps shown in Schemes 4–13 is a separate aspect of the invention, and where each of the intermediate compounds is a separate aspect of the present invention.

The synthetic methodology of Schemes 4–13 reacts an imine with a 9-DHB derivative having one or more protected hydroxyl groups. The imine may be generally represented by the formula Ar—CH=N-(protecting group). Ar represents an aryl group, e.g., phenyl as shown in Schemes 4–13. The protecting group is an amine protecting group, e.g., para-methoxyphenol as shown in Schemes 4–7, 10–11 and 12–13, or t-butoxycarbonyl as shown in Schemes 8–9. The 9-DHB derivative having one or more protected hydroxyl groups may have a free hydroxyl at C9 and a protected hydroxyl at C7, as illustrated in Schemes 4–7 and 8–9, or it may have both the C7 and C9 hydroxyl groups simultaneously protected as shown in Schemes 10–11 and 12–13. The preparation of 9-DHB derivatives having one or more protected hydroxyl groups has been described previously, in connection with Schemes 1–3.

For example, the present invention provides a method for producing a taxane intermediate, characterized in that a taxane represented by general formula III and formula IV:

FORMULA III

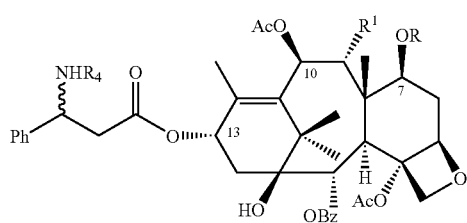

FORMULA IV

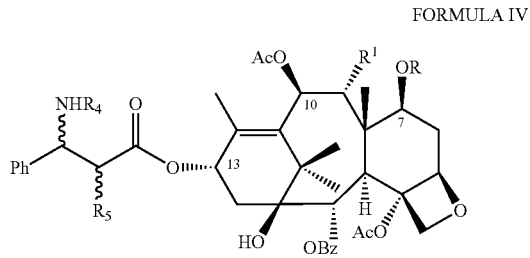

where R and $R_1$ simultaneously or independently represent a protective group for a hydroxyl group or $R_1$ is a carbonyl, $R_4$ represents a —$COR'_4$, —$COOR'_4$, —$CONHR'_4$, with $R'_4$ being a hydrocarbonyl, substituted hydrocarbonyl, or heterocyclo, more preferably $R_4$ represents a benzoyl group, a t-BOC group or an amine protecting group; and $R_5$ represent any protecting group that could be converted to a free hydroxyl group, is prepared using, as a starting material, a baccatin III compound represented by general formula I, Ia, II, and IIa, IIb, and IIc:

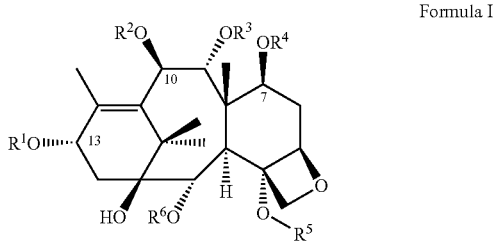

Formula I wherein $R^1$ is acetyl, $R^2$ is acetyl, $R^3$ is a hydroxyl protecting group, $R^4$ is a hydroxyl protecting group, $R^5$ is acetyl, and $R^6$ is benzoyl.

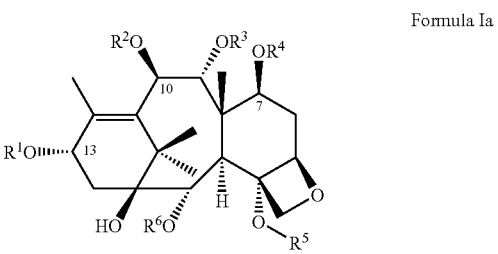

Formula Ia wherein $R^1$ is $XCH_2$—CO— and X is a halide, e.g., bromoacetyl, $R^2$ is acetyl, $R^3$ is a hydoxyl protecting group, $R^4$ is a hydroxyl protecting group, $R^5$ is acetyl, and $R^6$ is benzoyl.

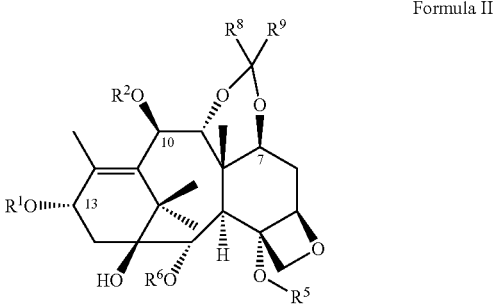

Formula II wherein $R^1$ is acetyl, $R^2$ is acetyl, $R^5$ is acetyl, $R^6$ is benzoyl, and $R^8$ and $R^9$ are independently selected from C1–C6 alkyl groups.

Formula IIa

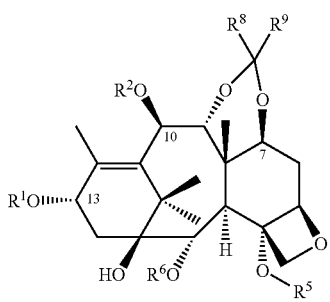

wherein $R^1$ is $XCH_2$—CO— and X is a halide, e.g., bromoacetyl, $R^2$ is acetyl, $R^5$ is acetyl, $R^6$ is benzoyl, and $R^8$ and $R^9$ are independently selected from C1–C6 alkyl groups.

Formula IIb

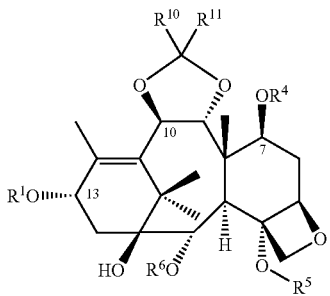

wherein $R^1$ is acetyl, $R^4$ is a hydroxyl protecting group, $R^5$ is acetyl, $R^6$ is benzoyl, and $R^{10}$ and $R^{11}$ are independently selected from $C_1$–$C_6$ alkyl groups.

Formula IIc

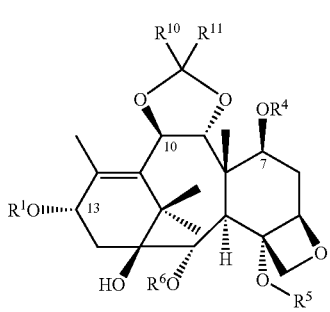

wherein $R^1$ is $XCH_2$—CO— and X is a halide, e.g., bromoacetyl, $R^4$ is a hydroxyl protecting group, $R^5$ is acetyl, $R^6$ is benzoyl, and $R^8$ and $R^9$ are independently selected from $C_1$–$C_6$ alkyl groups.

In formulae I, Ia, II, IIa, IIb and IIc, some preferred protecting groups are 2,2,2-trichloroethoxycarbonyl (troc), or a silyl group selected from trimethylsilyl, triethylsilyl, tripropylsilyl, dimethylethylsilyl, dimethylphenylsilyl, dimethyl(t-butyl)silyl, diethylmethyl silyl and diphenylmethylsilyl or dichloroacetyl.

In another exemplary aspect of the present invention, the taxane intermediate of formula III or IV may be obtained by reacting an anion of a baccatin III compound represented by formulae I, Ia, II and IIa formed in situ with an imine compound of the formula:

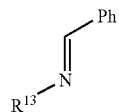

wherein $R^{13}$ is an amine protecting group, in the presences of a coupling agent, wherein the coupling agent is an alkali metal alkyl disilazide. The imine compound may optionally be obtained by reacting benzaldehyde with an amine, e.g., paramethoxy aniline to provide the imine having paramethoxy aniline as $R^{13}$, or ammonia to provide the imine having hydrogen as $R^{13}$, in a suitable solvent such as a chlorinated organic solvent. The alkali metal alkyl disilazide may optionally be selected from an alkali metal or alkaline earth metal base such as sodium hexamethyldisilazide, potassium hexamethyidisilazide, lithium hexamethyldisilazide, sodium diisopropylamide, potassium diisopropylamide, lithium diisopropylamide, sodium hydride, potassium hydride, lithium hydride, calcium hydride, magnesium hydride. The coupling reaction may optionally be performed in a dry nonprotic organic solvent such as tetrahydrofuran (THF), dioxane, ether, dimethoxyethane (DME), diglyme, dimethylformamide (DMF), mixtures of these solvents with hexane, toluene, and xylene. The coupling may be performed in a preferred temperature range at about –100° C. to about 50° C., more preferably at about –78° C. to about 25° C. This reaction is preferably carried out under inert atmosphere such as nitrogen or argon. In a preferred embodiment, at least one compound is LiHMDS, and/or the solvent used is an ether, more preferably tetrahydrofuran, and/or the reaction temperature is between –100° C. to 50° C. more preferably at –78 to about 25° C.

As another example, the present invention provides for the oxidation of a taxane intermediate, and more specifically a compound of the following formula,

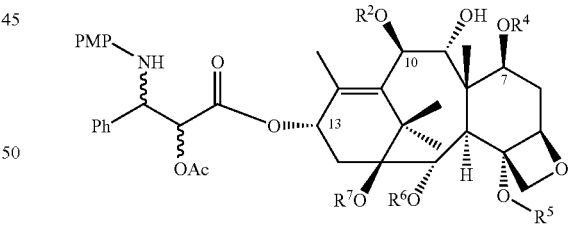

to provide the corresponding ketone of the formula

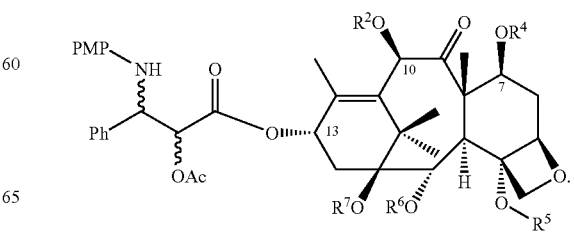

wherein $R^2$ is a hydroxyl protecting group and is preferably acetyl, $R^4$ is a hydroxyl protecting group, $R^5$ is a hydroxyl protecting group and is preferably acetyl, $R^6$ is a hydroxyl protecting group and is preferably benzoyl. The oxidation may be preformed using, for example, PDC or $CrO_3/H^+$. This oxidation is illustrated in the conversion of compound 18 to compound 19 in Scheme 4.

As another example, the present invention provides a taxane represented by general formula III and formula IV:

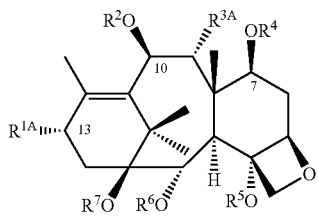

(III)

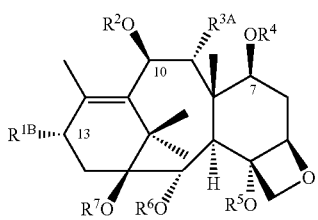

(IV)

wherein $R^{1A}$ represents the following structure,

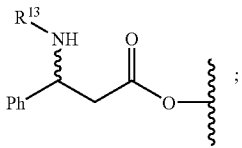

and $R^{1B}$ represents the following structure

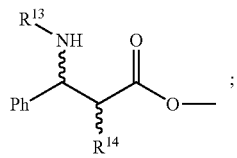

and the remaining R groups are defined as follows: $R^2$ is acetyl, $R^{3A}$ and $R^4$ simultaneously or independently represent a protective group for a hydroxyl group or $R^{3A}$ is a carbonyl, $R^5$ is acetyl, $R^6$ is benzoyl, $R^7$ is hydrogen, $R^{13}$ represents a hydrogen or an amine protecting group, where in one embodiment $R^{13}$ represents —$COR^{15}$, —$COOR^{15}$, or —$CONHR^{15}$, with $R^{15}$ being a hydrocarbonyl, substituted hydrocarbonyl, or heterocyclo, an in another preferred embodiment $R^{13}$ represents a benzoyl group or a t-BOC group; and $R^{14}$ represent any protecting group that could be converted to a free hydroxyl group. The taxanes of formula III and formula IV may be prepared according to methodology shown in Schemes 4–13.

The present invention also provides a method for producing a taxane intermediate represented by a general formula IV (as defined above) useful in producing taxol or taxotere, by using as a starting material a taxane intermediate of formula I, Ia, II, IIa, IIb or IIc as defined above, through intermediate compounds represented by general formulas III and IV as defined above.

Thus, in various aspects, the present invention provides the following:

A process comprising reacting an imine of formula Ph-CH=N—$R^{13}$ wherein $R^{13}$ represents hydrogen or an amine protecting group, with a C13 acetate ester of baccatin or a derivative or analog thereof of formulae

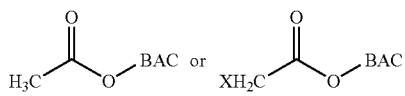

wherein X is a halogen, to provide a coupled product of formula

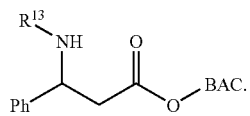

A process comprising treating a compound of the formula

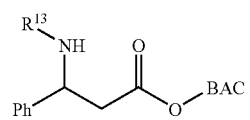

wherein $R^{13}$ represents hydrogen or an amine protecting group, under diazotiation conditions, to provide a compound of the formula

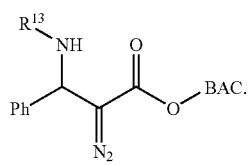

A process comprising treating a compound of the formula

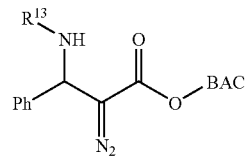

where $R^{13}$ is hydrogen or an amine protecting group, under conditions that convert a diazo group to an acetate group, to provide a compound of the formula

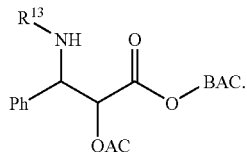

A process comprising treating a compound of the formula

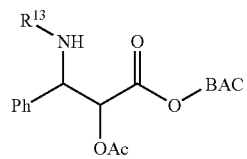

where $R^{13}$ represents hydrogen or an amine protecting group, under hydrolysis conditions that convert an acetate group to a hydroxyl group, or under conditions that convert the acetate group to an ethoxyethyl group and then convert the ethoxy ethyl group to a hydroxyl group, and provide a compound of the formula

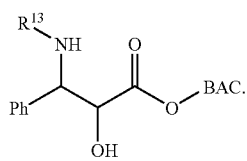

A process comprising treating a compound of the formula

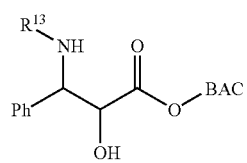

where $R^{13}$ is an amine protecting group, under conditions that remove an amine protecting group and provide a compound of the formula

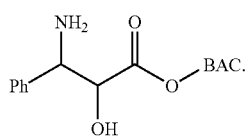

A process comprising treating a compound of the formula

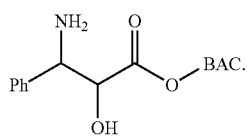

under conditions that introduce a protecting group ($R^{13}$) onto the amino group, such as a benzoyl group as shown in the following formula

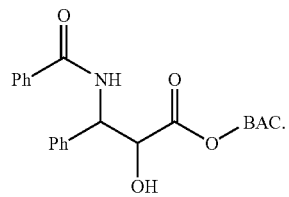

While benzoyl is shown in the above compound for illustrative purposes, and is the protecting group in one aspect of the present invention, other amine protecting groups may also be used. For instance, in another aspect, the protecting group is para-methoxyphenyl (PMP). In yet another aspect the protecting group is t-BOC.

In each of the above-mentioned processes, BAC may optionally be described by the following formula, wherein $R^4$ is a hydroxyl protecting group

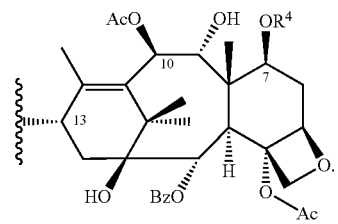

Alternatively, as illustrated in Scheme 10 (continuing to Scheme 11) and Scheme 12 (continuing to Scheme 13) BAC may be described by the following formula wherein $R^2$ is a hydroxyl protecting group, preferably acetyl, and $R^8$ and $R^9$ represent alkyl groups, e.g., C1–C10 alkyl groups such as methyl and ethyl,

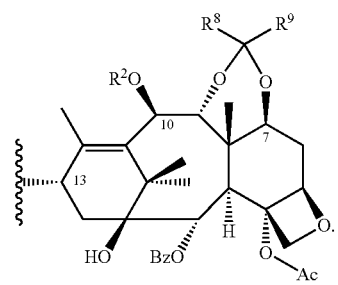

Alternatively, BAC may be described by the following formula wherein $R^4$ represents a hydroxyl protecting group, preferably dichloroacetyl, and $R^{10}$ and $R^{11}$ represent alkyl groups, e.g., C1–C10 alkyl groups such as methyl and ethyl,

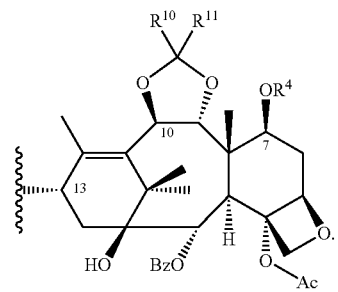

In Schemes 4–13, the baccatin compound has an acetoxy group at the C13 position. In one aspect, the present invention provides for the synthetic transformations shown in Schemes 4–13 where the baccatin compound has an acetoxy group at the C13 position. However, in another aspect, the present invention provides for the synthetic transformations shown in Schemes 4–13 where the baccatin compound has a haloacetoxy group at the C13 position, e.g., a chloroacetoxy group or a bromoacetoxy group.

Schemes 14 and 15

Schemes 14 and 15 teach additional aspects of the present invention. These Schemes teach the coupling of 9-DHB derivative, and more specifically 9-DHB derivatives that may be prepared as taught in Scheme 3, with a sidechain-precursor, e.g., a phenylisoserine compound or a beta-lactam. The coupling reaction adds, e.g., the phenylisoserine group to the C13 position of the 9-DHB derivative, to provide a synthetic route to taxol or taxotere. Alternatively, the coupling reaction reacts a beta-lactam with the C13 position of the 9-DHB derivative, to provide a synthetic route to taxol or taxotere.

Thus, in one aspect, the present invention provides a process of obtaining the compound of the following formulae (VII):

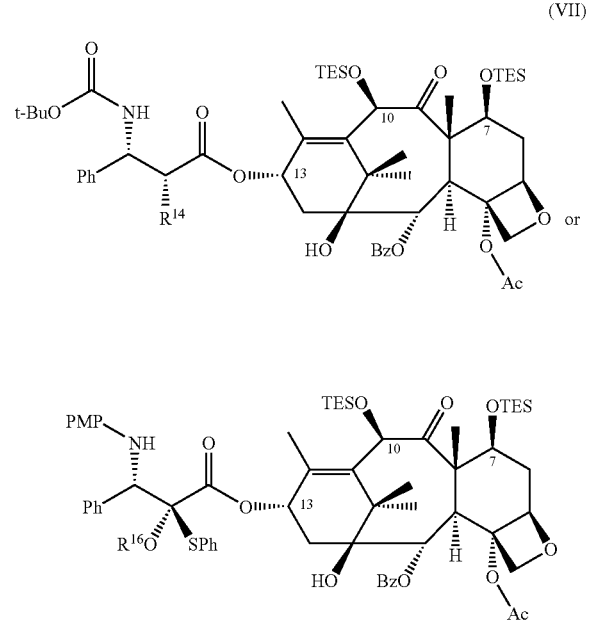

by reacting compound of formula V:

wherein $R^{14}$ is —SPh, —OAc, —OMe, —OEE, —O-t-BOC, or —C(O)CH$_2$Cl, and $R^{16}$ is acetyl or ethoxyethyl, with a compound of formula VI:

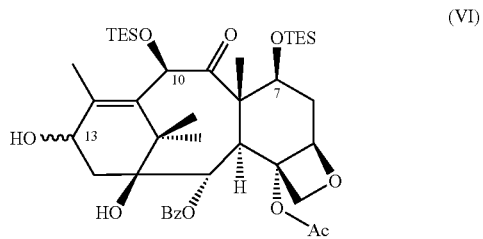

In another aspect, the process is extended to the conversion of the compound of formula VII to taxol or taxotere.

In yet another aspect, a beta-lactam having both a protected thiol group and a protected hydroxyl group at C3 of the beta-lactam ring, is coupled to the C13 position of a baccatin compound, e.g., a compound of formula VI. Such a beta-lactam compound may be prepared by a process wherein a halide substituent on a beta-lactam ring is replaced with a protected hydroxyl group, as illustrated by the following scheme

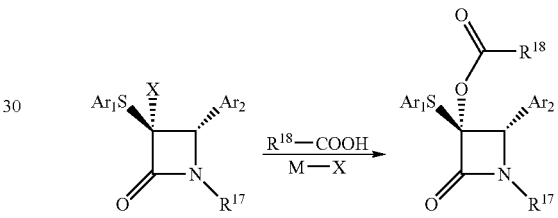

wherein $Ar_1$ and $Ar_2$ are each aryl groups, where each of $Ar_1$ and $Ar_2$ are independently optionally substituted with one or more of halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbon atoms, and aryloxycarbonyl where the aryloxy portion contains 6 to 20 carbon atoms; M is metal and X is one or more halides attached to the metal; $R^{17}$ is selected from hydrogen, benzoyl and tBOC; and $R^{18}$ is $C_1$–$C_6$ alkyl. In a preferred embodiment, $Ar_1$ and $Ar_2$ are each phenyl. For instance, a chloro-substituted beta-lactam may be converted into the corresponding beta-lactam where the chloride group is replaced with an acetate group. This conversion is illustrated in the following Reaction.

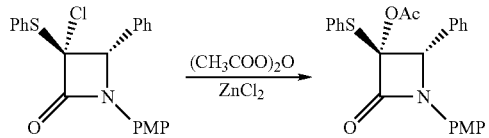

More specifically, the chloro-substituted beta-lactam is dissolved in an inert solvent, e.g., anhydrous dichloromethane, at room temperature under an inert atmosphere, e.g., argon atmosphere. To this stirred solution at room temperature is added sequentially silica gel, zinc chloride and an alkyl anhydride, e.g., acetic anhydride. The reaction mixture is left at this temperature for ca. 16 hrs and then worked up. The silica gel is filtered and the filtrate evaporated, dissolved in dichloromethane and worked up as usual for this type of reaction. The crude residue is purified by column chromatography using mixtures of hexanes/ethyl acetate to afford the pure product.

The halogenated beta-lactam used as the starting material in the above reaction may be prepared according to the following Reaction:

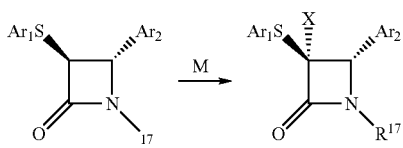

wherein $Ar_1$ and $Ar_2$ are each aryl groups, where each of $Ar_1$ and $Ar_2$ is independently optionally substituted with one or more of halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbon atoms, and aryloxycarbonyl where the aryloxy portion contains 6 to 20 carbon atoms; X is halide; $R^{17}$ is selected from hydrogen, benzoyl and tBOC, and M is a halogenating agent. In one embodiment, each of $Ar_1$ and $Ar_2$ is phenyl. Exemplary halogenating agents include, without limitation, inorganic acid halides, for example thionyl chloride, phosphorus trichloride, phosphorus tribromide, phosphoryl chloride trifluoromethanesulfonic acid, N-iodosuccinimide and phosphorus pentachloride. For example, a trans thiophenyl β-lactam can be modified by introducing a chloro group at the 3-position as shown in the following Reaction.

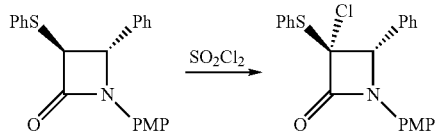

More specifically, a trans thiophenyl beta lactam is dissolved in an inert solvent, e.g., anhydrous dichloromethane, under an inert atmosphere, e.g., argon gas, and cooled to about 0° C. Sulfuryl chloride is added dropwise to the stirred solution at ca. 0° C. and left at this temperature for ca. 2 hrs. The solvent is evaporated and the residue dissolved in dichloromethane and washed successively with water, 10% sodium bicarbonate, saturated brine and dried over anhydrous sodium sulfate. After removal of the solvent under reduced pressure the crude solid is purified by recrystallization using mixtures of dichloromethane/hexanes to give the chloro group at the 3-position of the trans thiophenyl beta lactam.

The trans thiophenyl beta lactam used as a starting material in the above reaction may be prepared in a variety of ways. For instance, as shown in the following Reaction,

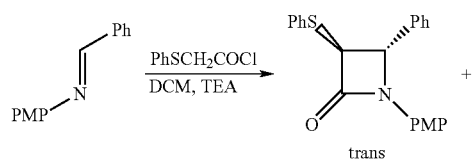

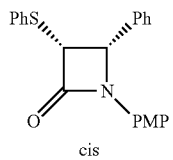

an imine (prepared by reaction between benzaldehyde and paramethoxyaniline) may be dissolved in an inert solvent such as dichloromethane and cooled to about 0° C. under an inert atmosphere such as argon gas. Thiophenyl acetyl chloride or any other respective acid chloride may be added dropwise to the cooled stirred solution of the imine at about 0° C. To the resulting solution may be added dropwise a tertiary amine, e.g., triethylamine, also at about 0° C. The reaction mixture is gradually warmed to room temperature and kept at this temperature for about 16 hours. The reaction may then be quenched by pouring into ice-cold water and extracted three times with dichloromethane and dried over anhydrous magnesium sulfate. The solvent may be evaporated to give the crude product which may be purified by column chromatography using dichloromethane initially followed by mixtures of hexane/ethyl acetate to get the pure cis and trans β-lactams. The cis and trans isomers may be separated from one another by, e.g., column chromatography. Alternatively, the thiophenyl-substituted beta-lactam may be prepared by reaction benzaldehyde with ammonia in the presence of PhS—CH$_2$—COCl.

Thus, as illustrated in Schemes 14 and 15, in one aspect the present invention provides a process comprising coupling a beta lactam of the formula

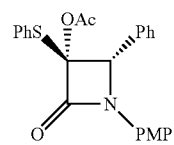

with a baccatin compound of the formula

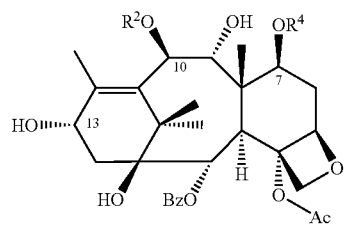

wherein $R^2$ and $R^4$ are both TES or dichloroacetyl, or $R^2$ is acetyl and $R^4$ is TES or dichloroacetyl. The coupling reaction is preferably preformed in the presence of a base, e.g., sodium hydride. For instance, the coupling reaction may be performed by combining the beta-lactam and the baccatin compound in the presence of sodium hydride and tetrahydrofuran at about −20 to about +25° C.

The following are additional aspects of the present invention, where the preparation of some of the following compounds is shown in Scheme 3:

A compound of the formula

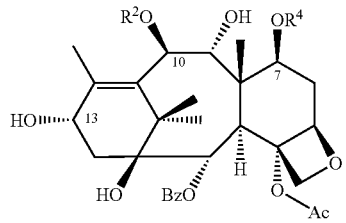

wherein $R^2$ and $R^4$ are identical and selected from triethylsilyl, dichloroacetyl, benzyloxycarbonyl, and 2,2,2-trichloroethoxycarbonyl.

A process comprising coupling a compound of formula

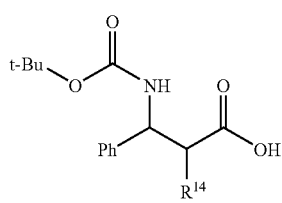

where $R^{14}$ is selected from —SPh, —OAc, —OMe, —OEE (—O-ethoxyethyl), —O-t-BOC, or —OC(O)CH$_2$Cl, with a compound of formula

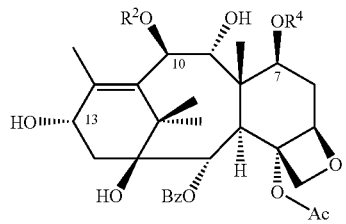

wherein $R^2$ and $R^4$ are identical and selected from triethylsilyl, dichloroacetyl, benzyloxycarbonyl, and 2,2,2-trichloroethoxycarbonyl, to provide a compound of formula

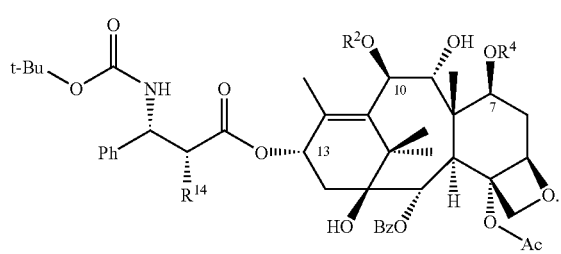

A compound of formula

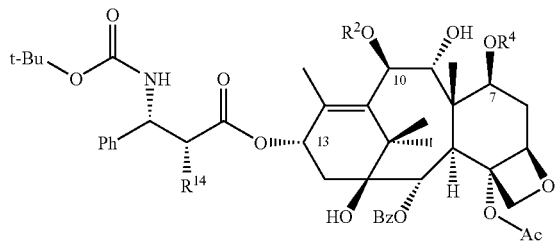

wherein $R^2$ and $R^4$ are identical and selected from triethylsilyl, dichloroacetyl, benzyloxycarbonyl, and 2,2,2-trichloroethoxycarbonyl.

A process comprising coupling a compound of formula

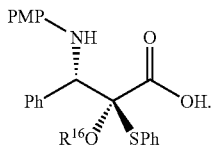

wherein $R^{16}$ is acetyl or ethoxyethyl, with a compound of formula

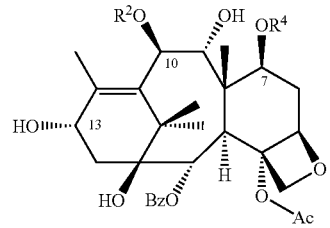

wherein $R^2$ and $R^4$ are identical and selected from triethylsilyl, dichloroacetyl, benzyloxycarbonyl, and 2,2,2-trichloroethoxycarbonyl, to provide a compound of formula

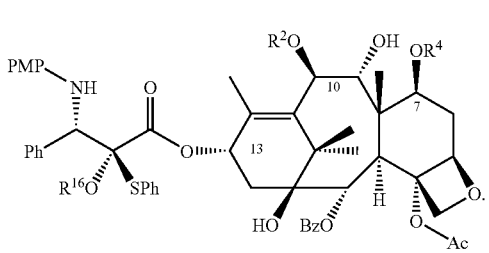

A compound of formula

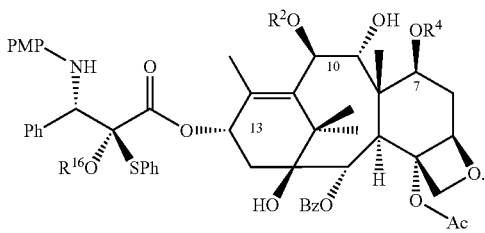

wherein $R^2$ and $R^4$ are identical and selected from triethylsilyl, dichloroacetyl, benzyloxycarbonyl, and 2,2,2-trichloroethoxycarbonyl, and $R^{16}$ is acetyl or ethoxyethyl.

A compound of formula

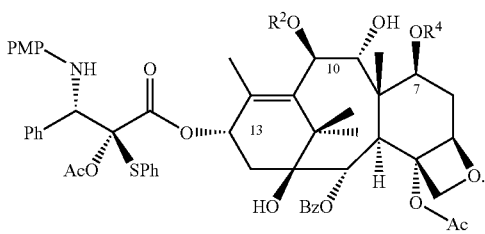

wherein $R^2$ and $R^4$ are identical and selected from triethylsilyl, dichloroacetyl, benzyloxycarbonyl, and 2,2,2-trichloroethoxycarbonyl.

A compound of formula

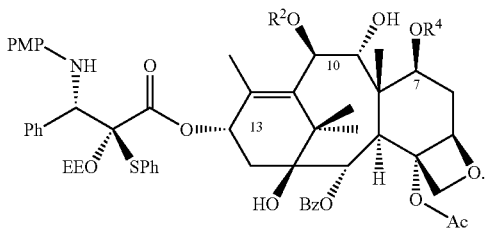

wherein $R^2$ and $R^4$ are identical and selected from triethylsilyl, dichloroacetyl, benzyloxycarbonyl, and 2,2,2-trichloroethoxycarbonyl, and EE represents ethoxyethyl.

A compound of the formula [compound 14.2]

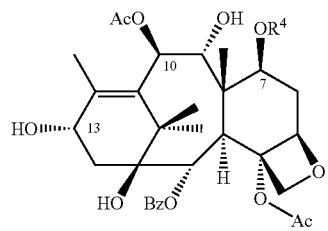

wherein $R^4$ is selected from triethylsilyl, dichloroacetyl, benzyloxycarbonyl, and 2,2,2-trichloroethoxycarbonyl.

A process comprising coupling a compound of formula

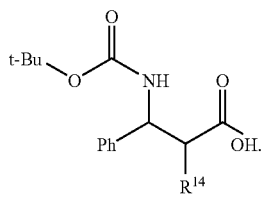

where $R^{14}$ is selected from —SPh, —OAc, —OMe, —OEE, —O-t-BOC, or —OC(O)CH$_2$Cl, with a compound of formula

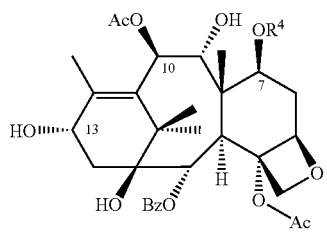

wherein $R^4$ is selected from triethylsilyl, dichloroacetyl, benzyloxycarbonyl, and 2,2,2-trichloroethoxycarbonyl, to provide a compound of formula

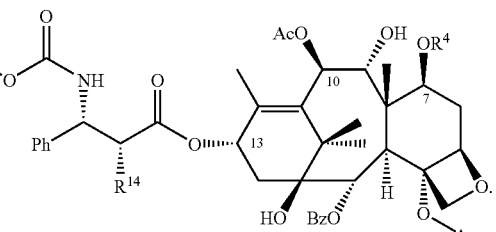

A compound of formula

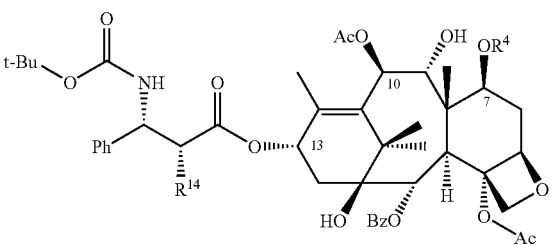

wherein $R^4$ is selected from triethylsilyl, dichloroacetyl, benzyloxycarbonyl, and 2,2,2-trichloroethoxyparbonyl, and $R^{16}$ is selected from —SPh, —OAc, —OMe, —OEE, —O-t-BOC, or —OC(O)CH$_2$Cl.

A process comprising coupling a compound of formula

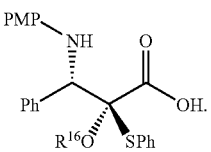

wherein $R^{16}$ represents acetyl or ethoxyethyl, with a compound of formula

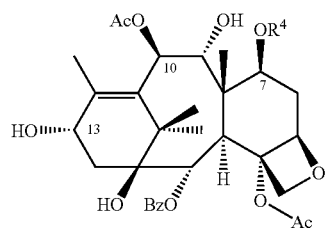

wherein $R^4$ is selected from triethylsilyl, dichloroacetyl, benzyloxycarbonyl, and 2,2,2-trichloroethoxycarbonyl, to provide a compound of formula

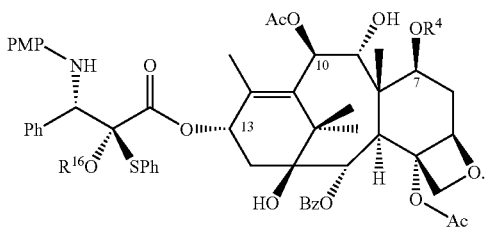

A compound of the formula

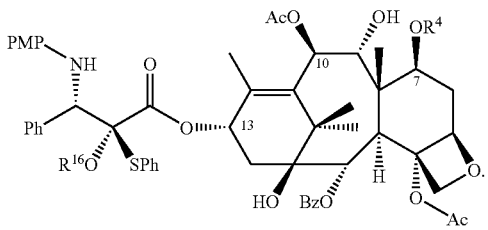

wherein $R^4$ is selected from triethylsilyl, dichloroacetyl, benzyloxycarbonyl, and 2,2,2-trichloroethoxycarbonyl, and $R^{16}$ is selected from acetyl and ethoxyethyl.

A compound of the formula

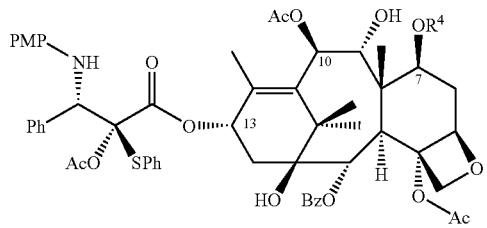

wherein $R^4$ is selected from triethylsilyl, dichloroacetyl, benzyloxycarbonyl, and 2,2,2-trichloroethoxycarbonyl.

A compound of the formula

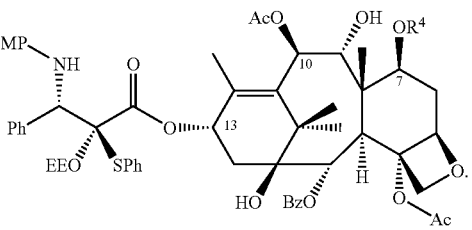

wherein $R^4$ is selected from triethylsilyl, dichloroacetyl, benzyloxycarbonyl, and 2,2,2-trichloroethoxycarbonyl, and EE represents ethoxyethyl.

A compound of the formula [compound 14.3]

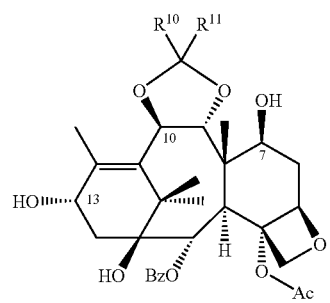

wherein $R^{10}$ and $R^{11}$ are independently selected from alkyl groups, e.g., $C_1$–$C_6$ alkyl groups, e.g., methyl.

A process comprising coupling a compound of formula

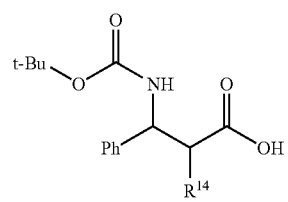

where $R^{14}$ is selected from —SPh, —OAc, —OMe, —OEE, —O-t-BOC, or —OC(O)CH$_2$Cl, with a compound of formula [compound 14.3]

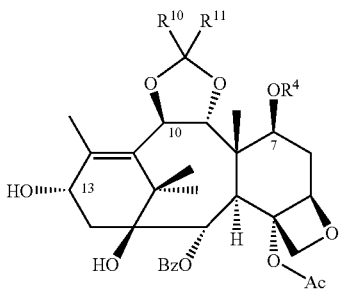

wherein $R^4$ is a hydrogen or a protected hydroxyl group, preferably hydrogen, and $R^{10}$ and $R^{11}$ are independently selected from alkyl groups, to provide a compound of formula

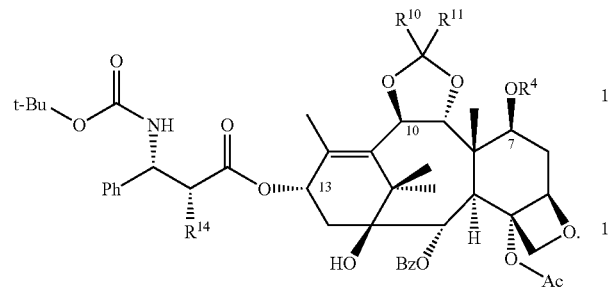

A compound of the formula

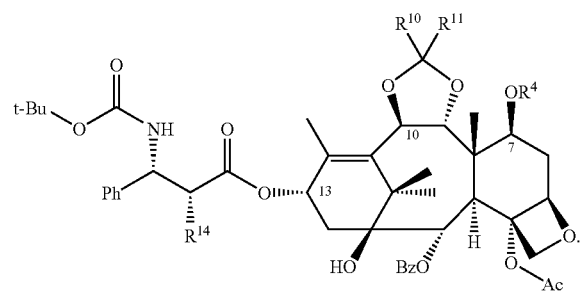

Wherein $R^4$ is hydrogen or a hydroxyl protecting group, preferably hydrogen, $R^{10}$ and $R^{11}$ are independently selected from alkyl groups, and $R^{14}$ is selected from —SPh, —OAc, —OMe, —OEE, —O-t-BOC, or —OC(O)CH$_2$Cl.

A process comprising coupling a compound of formula

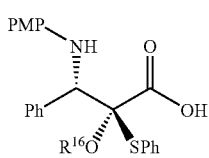

where $R^{16}$ is acetyl or ethoxyethyl, with a compound of formula [compound 14.3]

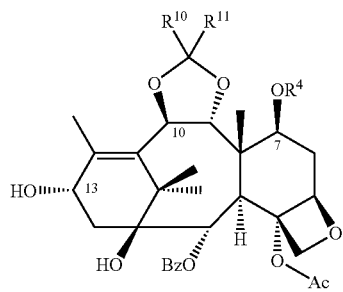

wherein $R^4$ is hydrogen or a hydroxyl protecting group, preferably hydrogen, and $R^{10}$ and $R^{11}$ are independently selected from alkyl groups, to provide a compound of formula

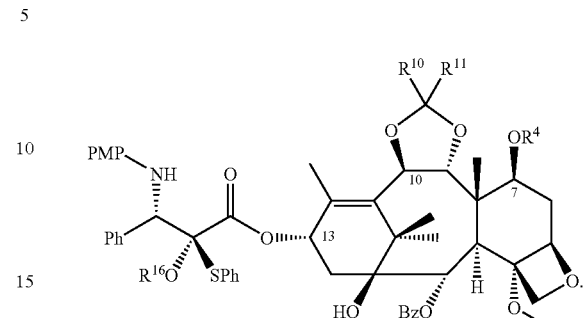

A compound of formula

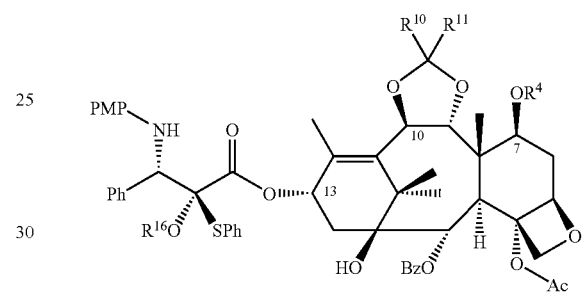

wherein $R^4$ is hydrogen or a hydroxyl protecting group, preferably hydrogen, $R^{10}$ and $R^{11}$ are independently selected from alkyl groups, and $R^{16}$ is acetyl or ethoxyethyl.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:
1. A compound of the formula

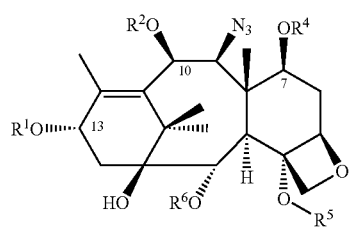

wherein $R^1$, $R^2$, $R^4$, $R^5$ and $R^6$ each represent hydrogen or a hydroxyl protecting group, independently selected at each location.

2. The compound of claim 1 wherein $R^1$, $R^2$, $R^4$, $R^5$ and $R^6$ each represent a hydroxyl protecting group.

3. The compound of claim 1 wherein each of $R^1$, $R^2$, $R^4$, $R^5$ and $R^6$ is, independently at each location, formyl, acetyl, dichloroacetyl, propionyl, isopropionyl, pivalyl, trimethylsilyl, triethylsilyl, triisopropylsilyl, dimethylisopropylsilyl, diethylisopropylsilyl, tert-butyldimethylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, t-butyloxycarbonyl, benzyloxycarbonyl, methoxymethyl, methoxyethyl, ethoxyethyl, para-methoxyphenyl, tetrahydropyranyl, tetrahydrofuranyl, alkylsulfonyl or arylsulfonyl.

4. The compound of claim 1 wherein $R^1$ is acetyl, $R^2$ is acetyl, $R^4$ is a hydroxyl protecting group, $R^5$ is acetyl, and $R^6$ is benzoyl.

5. A method comprising reacting a compound of the formula

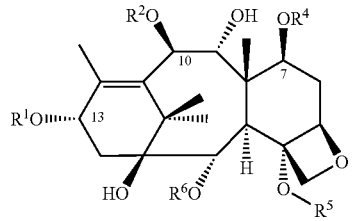

by a Mitsunobu displacement reaction using an azide compound, so as to provide a compound of the formula

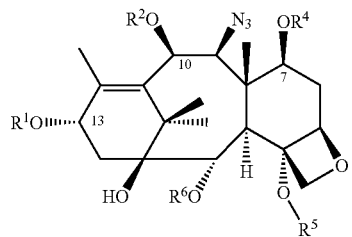

wherein $R^1$, $R^2$, $R^4$, $R^5$ and $R^6$ each represent hydrogen or a hydroxyl protecting group, independently selected at each location.

6. A process comprising oxidizing a compound of the formula

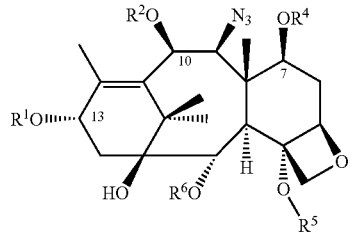

to provide a compound of the formula

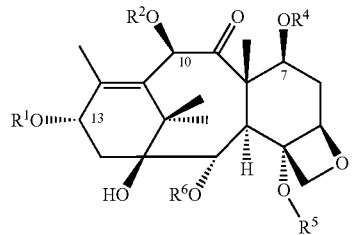

wherein $R^1$, $R^2$, $R^4$, $R^5$ and $R^6$ each represent a hydroxyl protecting group, independently selected at each location.

7. The process of claim 6 wherein the azide is converted to a carbonyl compound by using an alkoxide in THF, most preferably either LiOMe or NaOMe followed by acidic hydrolysis.

8. A compound of the formula

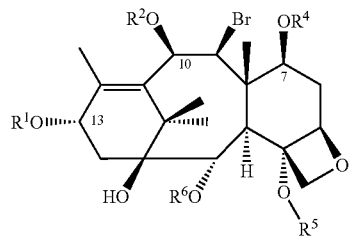

wherein $R^1$, $R^2$, $R^4$, $R^5$ and $R^6$ each represent hydrogen or a hydroxyl protecting group, independently selected at each location.

9. The compound of claim 8 wherein $R^1$, $R^2$, $R^5$ and $R^6$ each represent a hydroxyl protecting group, and $R^4$ is hydrogen.

10. The compound of claim 8 wherein each of $R^1$, $R^2$, $R^5$ and $R^6$ is, independently at each location, formyl, acetyl, dichloroacetyl, propionyl, isopropionyl, pivalyl, trimethylsilyl, triethylsilyl, triisopropylsilyl, dimethylisopropylsilyl, diethylisopropylsilyl, tert-butyldimethylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, t-butyloxycarbonyl, benzyloxycarbonyl, methoxymethyl, methoxyethyl, ethoxyethyl, para-methoxyphenyl, tetrahydropyranyl, tetrahydrofuranyl, alkylsulfonyl or arylsulfonyl.

11. The compound of claim 8 wherein $R^1$ is acetyl, $R^2$ is acetyl, $R^4$ is hydrogen, $R^5$ is acetyl, and $R^6$ is benzoyl.

12. A process comprising bromination of a compound of the formula

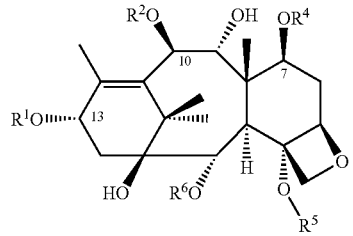

to provide a compound of the formula

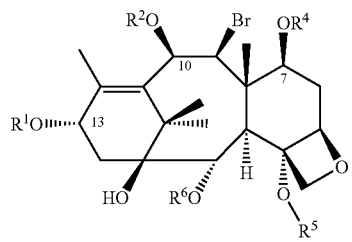

wherein $R^1$, $R^2$, $R^4$, $R^5$ and $R^6$ each represent hydrogen or a hydroxyl protecting group, independently selected at each location.

13. The process of claim 12 wherein the bromination comprises use of a brominating agent.

14. The process of claim 12 wherein the compound of the formula

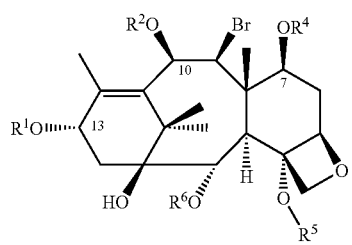

is in admixture with a compound of formula

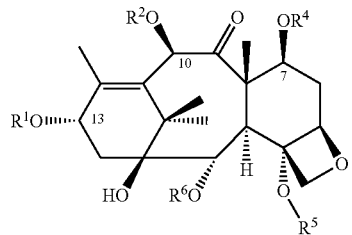

wherein $R^1$, $R^2$, $R^4$, $R^5$ and $R^6$ each represent hydrogen or a hydroxyl protecting group, independently selected at each location.

15. A process comprising oxidation of a compound of the formula

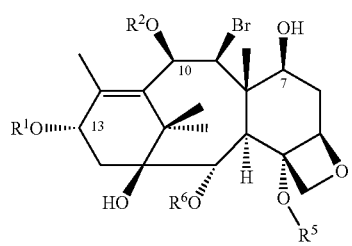

to provide a compound of the formula

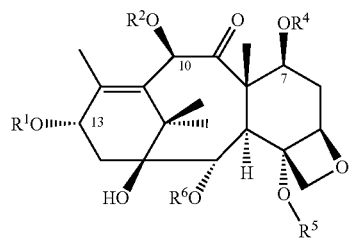

wherein $R^1$, $R^2$, $R^4$, $R^5$ and $R^6$ each represent hydrogen or a hydroxyl protecting group, independently selected at each location.

16. The process of claim 15 wherein a bromide is converted to an azide and the azide is converted to a carbonyl.

17. A process comprising treating a starting compound of the formula

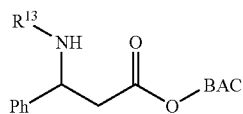

wherein $R^{13}$ represents hydrogen or an amine protecting group, under diazotiation conditions, to provide a product compound of the formula

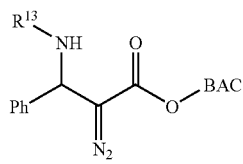

wherein BAC is

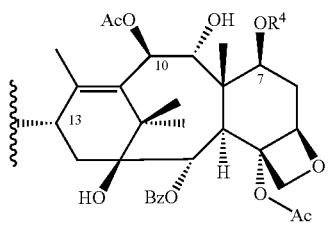

wherein $R^4$ is a hydrogen protecting group,

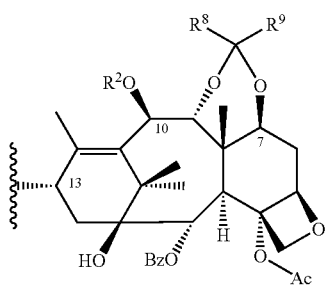

wherein $R^2$ is a hydroxyl protecting group, preferably acetyl, and $R^8$ and $R^9$ represent alkyl groups, e.g., C1–C10 alkyl groups such as methyl and ethyl, or

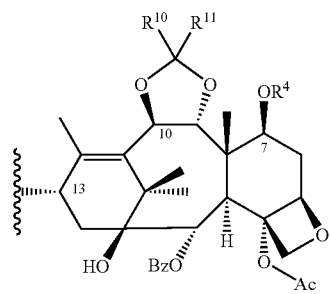

wherein $R^4$ represents a hydroxyl protecting group, preferably dichloroacetyl, and $R^{10}$ and $R^{11}$ represent alkyl groups, e.g., C1–C10 alkyl groups such as methyl and ethyl, wherein the diazotiation conditions comprise tosyl azide and at least base selected from triethylamine and diazobicycloundecane.

18. A process comprising treating a compound of the formula

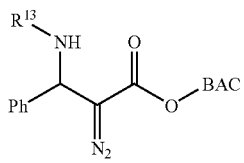

where $R^{13}$ is hydrogen or an amine protecting group, under conditions that convert a diazo group to an acetate group, to provide a compound of the formula

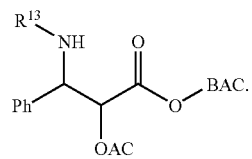

19. A process comprisina enolate oxidation of a starting compound of the formula

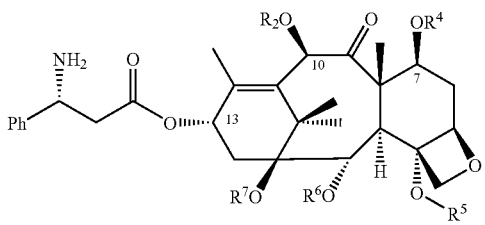

to provide a product compound of the formula

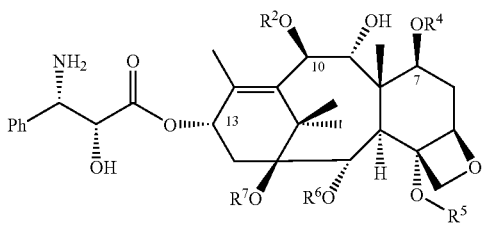

wherein $R^2$ is a hydroxyl protecting group, $R^4$ is hydrogen or a hydroxyl protecting group, $R^5$ is a hydroxyl protecting group, $R^6$ is a hydroxyl protecting group, and $R^7$ is hydrogen or a hydroxyl protecting group, wherein the starting compound is exposed to oxidizing conditions comprising potassium hexamethyldisilazide and a molybdenum compound.

* * * * *